United States Patent
Sugawara et al.

(10) Patent No.: US 11,912,688 B2
(45) Date of Patent: Feb. 27, 2024

(54) 1, 3-DIOXOLANE DERIVATIVE

(71) Applicant: TOHOKU UNIVERSITY, Sendai (JP)

(72) Inventors: Akira Sugawara, Miyagi (JP); Atsushi Yokoyama, Miyagi (JP); Susumu Suzuki, Miyagi (JP); Yoshiharu Iwabuchi, Miyagi (JP); Takayuki Doi, Miyagi (JP)

(73) Assignee: Tohoku University, Miyagi (JP)

( * ) Notice: Subject to any disclaimer, the term of this patent is extended or adjusted under 35 U.S.C. 154(b) by 237 days.

(21) Appl. No.: 17/430,884

(22) PCT Filed: Feb. 14, 2020

(86) PCT No.: PCT/JP2020/005858
§ 371 (c)(1),
(2) Date: Aug. 13, 2021

(87) PCT Pub. No.: WO2020/166710
PCT Pub. Date: Aug. 20, 2020

(65) Prior Publication Data
US 2022/0033386 A1 Feb. 3, 2022

(30) Foreign Application Priority Data
Feb. 15, 2019 (JP) .................. 2019-025963

(51) Int. Cl.
*C07D 405/06* (2006.01)
*A61P 13/02* (2006.01)

(52) U.S. Cl.
CPC ............ *C07D 405/06* (2013.01); *A61P 13/02* (2018.01)

(58) Field of Classification Search
CPC ............................... C07D 405/06; A61P 13/02
See application file for complete search history.

(56) References Cited

U.S. PATENT DOCUMENTS

| | | | | |
|---|---|---|---|---|
| 3,936,470 A | * | 2/1976 | Heeres | C07D 303/08 549/453 |
| 4,101,664 A | | 7/1978 | Heeres | |
| 4,338,327 A | * | 7/1982 | Heeres | C07D 249/08 514/383 |
| 2005/0187269 A1 | | 8/2005 | Kuroita et al. | |
| 2018/0243271 A1 | | 8/2018 | Fukui et al. | |

FOREIGN PATENT DOCUMENTS

| | | |
|---|---|---|
| CN | 104774195 A | 7/2015 |
| JP | 51-100073 A | 9/1976 |
| JP | 55-069579 A | 5/1980 |
| JP | 59-139380 A | 8/1984 |
| JP | 2002-535328 A | 10/2002 |
| JP | 2012-031135 A | 2/2012 |
| JP | 2015-534977 A | 12/2015 |
| JP | 2017-008081 A | 1/2017 |
| JP | 2017-198689 A | 11/2017 |
| JP | 2019-099550 A | 6/2019 |
| WO | WO-00/43390 A1 | 7/2000 |
| WO | WO-2010/114801 A1 | 10/2010 |
| WO | WO-2013/123305 A1 | 8/2013 |
| WO | WO-2014/064566 A1 | 5/2014 |
| WO | WO-2016/190420 A1 | 12/2016 |

* cited by examiner

*Primary Examiner* — Theodore R. Howell
(74) *Attorney, Agent, or Firm* — Foley & Lardner LLP

(57) ABSTRACT

The present invention provides a compound represented by chemical formula (I) or a pharmaceutically acceptable salt thereof, and a pharmaceutical composition containing the same.

9 Claims, 19 Drawing Sheets

Specification includes a Sequence Listing.

WT iNOS

D-532

PAS-POSITIVE AREA RATIO IN GLOMERULI

Lepr$^{db/m+}$ + Vehicle

Lepr$^{db/db}$ + Vehicle

Lepr$^{db/db}$ + D-532

Lepr^(db/db) + Vehicle

Lepr^(db/db) + Vehicle

Lepr^(db/db) + D-532

SEQUENCE LISTING

<160> NUMBER OF SEQ ID NOS: 6

<210> SEQ ID NO 1
<211> LENGTH: 36
<212> TYPE: DNA
<213> ORGANISM: Artificial Sequence
<220> FEATURE:
<223> OTHER INFORMATION: Forwrd Primer

<400> SEQUENCE: 1
atgcatctcg agatggcgcg cgcgctggcg gatcta                      36

<210> SEQ ID NO 2
<211> LENGTH: 38
<212> TYPE: DNA
<213> ORGANISM: Artificial Sequence
<220> FEATURE:
<223> OTHER INFORMATION: Reverse Primer

<400> SEQUENCE: 2
atgcatgcgg ccgcttataa tggtctcccc agggtgcc                    38

<210> SEQ ID NO 3
<211> LENGTH: 18
<212> TYPE: DNA
<213> ORGANISM: Artificial Sequence
<220> FEATURE:
<223> OTHER INFORMATION: Forward Primer

<400> SEQUENCE: 3
tctgcagatc gcgtggag                                          18

<210> SEQ ID NO 4
<211> LENGTH: 19
<212> TYPE: DNA
<213> ORGANISM: Artificial Sequence
<220> FEATURE:
<223> OTHER INFORMATION: Reverse Primer

<400> SEQUENCE: 4
cttgtcccgg catagcaac                                         19

<210> SEQ ID NO 5
<211> LENGTH: 22
<212> TYPE: DNA
<213> ORGANISM: Artificial Sequence
<220> FEATURE:
<223> OTHER INFORMATION: Forward Primer

<400> SEQUENCE: 5
gtcagtgtcc ctggctccaa ga                                     22

<210> SEQ ID NO 6
<211> LENGTH: 22
<212> TYPE: DNA
<213> ORGANISM: Artificial Sequence
<220> FEATURE:
<223> OTHER INFORMATION: Reverse Primer

<400> SEQUENCE: 6
agctcatctc agagctcgtc cg                                     22

1, 3-DIOXOLANE DERIVATIVE

CROSS-REFERENCE TO RELATED APPLICATIONS

This application is the U.S. National Stage of PCT/JP2020/005858, filed Feb. 14, 2020, which claims priority to JP 2019-025963, filed Feb. 15, 2019.

The instant application contains a Sequence Listing which has been submitted in ASCII format via EFS-WEB and is hereby incorporated by reference in its entirety. Said ASCII copy, created on Aug. 12, 2021, is named sequence.txt and is 1,378 bytes.

TECHNICAL FIELD

The present invention relates to a 1,3-dioxolane derivative, in particular a 2-phenyl-1,3-dioxolane derivative, and a pharmaceutically acceptable salt thereof. Moreover, the present invention relates to a pharmaceutical composition containing the compound or a salt thereof.

BACKGROUND ART

The number of patients requiring hemodialysis is increasing steadily in recent years, which is recognized to be a social problem. Its causative diseases are chronic kidney diseases (CKDs) including diabetic nephropathy, chronic glomerulonephritis, and nephrosclerosis, and the execution of a comprehensive and effective measure against CKDs has been required to achieve a significant decrease in the number of patients introducing dialysis newly.

Among them, diabetic nephropathy (DN) is a kidney disease which influences up to a maximum of 40% of type I or type II diabetics, and advances due to diabetes. DN is characterized by a progressive decrease in a renal function which results in albuminuria (protein in urine) and end-stage renal disease (ESRD), hypertension, and increases in the cardiovascular morbidity and the mortality. ESRD is a fatal symptom of a complete or almost complete loss of the kidney function, which requires dialysis or kidney transplantation. Research of means for treating chronic kidney disease has been reported (Patent Literatures 1 to 4).

A compound having a 2-phenyl-1,3-dioxolane derivative is also used as a synthetic intermediate in addition to a use as an antifungal agent (Patent Literature 5).

CITATION LIST

Patent Literature

PTL 1: Japanese Patent Laid-Open No. 2017-198689
PTL 2: Japanese Patent Laid-Open No. 2017-008081
PTL 3: International Publication No. WO 2016/190420
PTL 4: Japanese Translation of PCT International Application Publication No. 2015-534977
PTL 5: Japanese Translation of PCT International Application Publication No. 2002-535328

DISCLOSURE OF INVENTION

Technical Problem

In one aspect, an object of the present invention is to provide a new 1,3-dioxolane derivative, in particular a 2-phenyl-1,3-dioxolane derivative, and a pharmaceutically acceptable salt thereof. Moreover, an object of the present invention is to provide a pharmaceutical composition containing the compound.

Solution to Problem

The present inventors have investigated earnestly to achieve the above-mentioned object and have completed the following present invention. The disclosure of the present specification includes inventions described in the following [1] to [10].

[1] A compound represented by chemical formula (I):

[Chemical Formula 1]

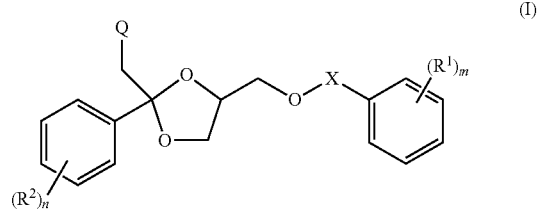

(I)

wherein $R^1$ and $R^2$ are each independently selected from a halogen atom, hydroxy, $C_{1-6}$ alkyl, and $C_{1-6}$ alkoxy;
m and n are each independently an integer selected from 0 to 5;
X is —$CH_2$— or —$C(=O)$—; and
Q is nitrogen-containing 5 to 9-membered heteroaryl attaching via a ring nitrogen atom, or a pharmaceutically acceptable salt thereof.

[2] The compound according to [1], wherein Q is nitrogen-containing 5-membered heteroaryl or nitrogen-containing 5-membered heteroaryl condensed with a benzene ring, the heteroaryl attaching via a ring nitrogen atom, or a pharmaceutically acceptable salt thereof.

[3] The compound according to [1] or [2], wherein X is —$CH_2$—, or a pharmaceutically acceptable salt thereof.

[4] The compound according to any one of [1] to [3], wherein the compound is represented by chemical formula (Ia):

[Chemical Formula 2]

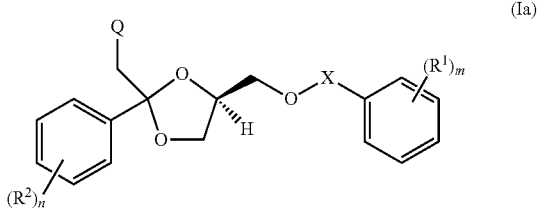

(Ia)

wherein $R^1$, $R^2$, m, n, and Q are as already defined,
or a pharmaceutically acceptable salt thereof.

[5] The compound according to any one of [1] to [4], wherein n is an integer selected from 0 to 2, and $R^2$ is a halogen atom, or a pharmaceutically acceptable salt thereof.

[6] The compound according to any one of [1] to [5], wherein m is 0, or a pharmaceutically acceptable salt thereof.

[7] The compound according to any one of [1] to [6], wherein Q is 1,2,3-benzotriazol-1-yl, 1,2,4-triazol-1-yl, or imidazolyl-1-yl, or a pharmaceutically acceptable salt thereof.

[8] The compound according to [1], wherein the compound is selected from:
1-(((2S,4S)-4-((benzyloxy)methyl)-2-phenyl-1,3-dioxolan-2-yl)methyl)-1H-benzo[d][1,2,3]triazole;
1-(((4S)-4-((benzyloxy)methyl)-2-phenyl-1,3-dioxolan-2-yl)methyl)-1H-1,2,4-triazole;
1-(((2S,4S)-4-((benzyloxy)methyl)-2-(4-chlorophenyl)-1,3-dioxolan-2-yl)methyl)-1H-1,2,4-triazole;
1-(((2S,4S)-4-((benzyloxy)methyl)-2-(2,4-dichlorophenyl)-1,3-dioxolan-2-yl)methyl)-1H-1,2,4-triazole;
1-(((2R,4S)-4-((benzyloxy)methyl)-2-(4-chlorophenyl)-1,3-dioxolan-2-yl)methyl)-1H-1,2,4-triazole;
1-(((2S,4S)-4-((benzyloxy)methyl)-2-(4-chlorophenyl)-1,3-dioxolan-2-yl)methyl)-1H-imidazole;
1-(((2S,4S)-4-((benzyloxy)methyl)-2-(2,4-dichlorophenyl)-1,3-dioxolan-2-yl)methyl)-1H-imidazole;
1-(((4S)-4-((benzyloxy)methyl)-2-phenyl-1,3-dioxolan-2-yl)methyl)-1H-imidazole;
1-(((4S)-4-((benzoyloxy)methyl)-2-(2,4-dichlorophenyl)-1,3-dioxolan-2-yl)methyl)-1H-1,2,4-triazole; and
1-(((2R,4S)-4-((benzyloxy)methyl)-2-(4-chlorophenyl)-1,3-dioxolan-2-yl)methyl)-1H-imidazole,
or a pharmaceutically acceptable salt thereof.

[9] A pharmaceutical composition comprising the compound according to any one of [1] to [8] or a pharmaceutically acceptable salt thereof.

[10] The pharmaceutical composition according to [9], for use in treating chronic kidney disease.

[11] The pharmaceutical composition according to [9] for use in treating a disease selected from diabetic nephropathy, glomerular injury, tubular injury, renal injury accompanying advanced age or related to dialysis, nephrosclerosis, nephrotoxicity, renal ischemia, primary vesicoureteral reflux, glomerulosclerosis, IgA-induced nephropathy, and hypertension-induced nephropathy.

[12] A method for treating chronic kidney disease, comprising administering a therapeutically effective amount of the compound according to any one of [1] to [8] or a pharmaceutically acceptable salt thereof to a subject in need thereof.

[13] A method for treating a disease, comprising administering a therapeutically effective amount of the compound according to any one of [1] to [8] or a pharmaceutically acceptable salt thereof to a subject in need thereof, wherein the disease is selected from diabetic nephropathy, glomerular injury, tubular injury, renal injury accompanying advanced age or related to dialysis, nephrosclerosis, nephrotoxicity, renal ischemia, primary vesicoureteral reflux, glomerulosclerosis, IgA-induced nephropathy, and hypertension-induced nephropathy.

Advantageous Effects of Invention

In one aspect, according to the present invention, a 2-phenyl-1,3-dioxolane derivative which has pharmacological activity, and can be used as an active ingredient of a medicament is provided. In another aspect, according to the present invention, means for treating chronic kidney disease is provided.

DESCRIPTION OF EMBODIMENTS

Figure 1:
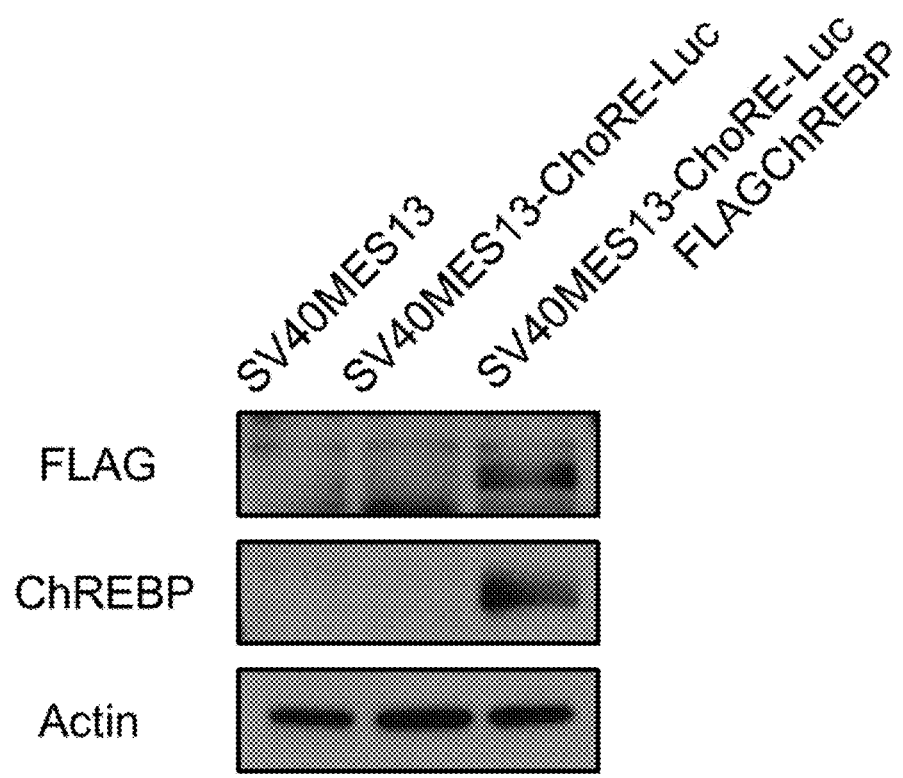
FIG. 1 shows the results of the Western blotting analysis of proteins derived from the cells SV40MES13, SV40MES13MES13ChoRE #4, and SV40MES13-ChoRE-Luc_FLAG-ChREBP. In the SV40MES 13-ChoRE-Luc_FLAG-ChREBP cells, anti-FLAG antibody (Merck KGaA)- and anti-ChREBP antibody (Novus Biologicals, LLC)-positive bands were confirmed, and the expression of ChREBP protein derived from pQCXIH FLAG ChREBP was confirmed.

Hereinafter, the present invention will be described further specifically.

As used herein, the "$C_{1-6}$ alkyl" means a linear, branched, cyclic, or partially cyclic alkyl group having 1 to 6 carbon atoms. Examples thereof include methyl, ethyl, n-propyl, i-propyl, n-butyl, s-butyl, i-butyl, t-butyl, n-pentyl, 3-methylbutyl, 2-methyl butyl, 1-methylbutyl, 1-ethylpropyl, n-hexyl, 4-methylpentyl, 3-methylpentyl, 2-methylpentyl, 1-methylpentyl, 3-ethylbutyl, 2-ethylbutyl, cyclopropyl, cyclobutyl, cyclopentyl, cyclohexyl, and cyclopropyl methyl. Examples thereof also include $C_{1-4}$ alkyl and $C_{1-3}$ alkyl.

As used herein, the "$C_{1-6}$ alkoxy" means an alkyloxy group with the alkyl group having 1 to 6 carbon atoms and already defined as an alkyl moiety [—O—($C_{1-6}$ alkyl)]. Examples thereof include methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, cyclopentyloxy, cyclohexyloxy, and cyclopropylmethyloxy. Examples thereof also include $C_{1-4}$ alkoxy and $C_{1-3}$ alkoxy.

As used herein, the "halogen atom" means a halogen atom such as a fluorine atom, a chlorine atom, a bromine atom, or an iodine atom as a substituent.

As used herein, the "nitrogen-containing 5 to 9-membered heteroaryl attaching via a nitrogen atom" means nitrogen-containing 5 to 9-membered heteroaryl bound to $CH_2$ through the ring nitrogen atom. The heteroaryl group may contain one or more heteroatoms selected from an oxygen atom, a nitrogen atom, and a sulfur atom in addition to the nitrogen atom at the binding point. Examples thereof include 1-pyrrolyl, 1-pyrazolyl, 1-imidazolyl, 1,2,4-triazol-1-yl, 1,2,4-triazol-4-yl, 1-tetrazolyl, 1-indolyl, 2-isoindolyl, 1-indazolyl, 2-indazolyl, 1-benzimidazole, 1,2,3-benzotriazol-1-yl, and purin-7-yl.

As used herein, the "nitrogen-containing 5-membered heteroaryl attaching via a nitrogen atom" means nitrogen-containing 5-membered heteroaryl bound to $CH_2$ through the ring nitrogen atom. The heteroaryl group may contain one or more heteroatoms selected from an oxygen atom, a nitrogen atom, and a sulfur atom in addition to the nitrogen atom at the binding point. Examples thereof include 1-pyrrolyl, 1-pyrazolyl, 1-imidazolyl, 1,2,4-triazol-1-yl, 1,2,4-triazol-4-yl, and 1-tetrazolyl.

As used herein, the "nitrogen-containing 5-membered heteroaryl attaching via a nitrogen atom" means nitrogen-containing 5-membered heteroaryl bound to $CH_2$ through the ring nitrogen atom. The heteroaryl group may contain one or more heteroatoms selected from an oxygen atom, a nitrogen atom, and a sulfur atom in addition to the nitrogen atom at the binding point. Examples thereof include 1-pyrrolyl, 1-pyrazolyl, 1-imidazolyl, 1,2,4-triazol-1-yl, 1,2,4-triazol-4-yl, and 1-tetrazolyl.

Examples of the halogen atom include a fluorine atom, a chlorine atom, a bromine atom, and an iodine atom.

In chemical formula (I), when m is 0, it is meant that $R^1$ is absent, and when n is 0, it is meant that $R^2$ is absent.

When the compound of chemical formula (I) or a pharmaceutically acceptable salt thereof forms a solvate such as a hydrate, the present invention can be implemented using the solvate. Moreover, the compound of the present invention or a pharmaceutically acceptable salt thereof can be implemented as appropriate as a mixture, a solution, crystal polymorphism, or the like.

As the compound of the present invention, compounds described in the Examples herein can be used, and more specifically, the following compounds can be used.

As long as the "pharmaceutically acceptable salt" of the compound of chemical formula (I) is a salt which can be used as a medicament, the "pharmaceutically acceptable salt" of the compound of chemical formula (I) is not particularly limited. Examples of a salt which the compound of the present invention forms with a base include salts with inorganic bases such as sodium, potassium, magnesium, calcium, and aluminum; and salts with organic bases such as methylamine, ethylamine, and ethanolamine. The salt may be an acid addition salt. Specific examples of such a salt include acid addition salts with mineral acids such as hydrochloric acid, hydrobromic acid, hydroiodic acid, sulfuric acid, nitric acid, and phosphoric acid; and with organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid.

Each of atoms (for example, a hydrogen atom, a carbon atom, an oxygen atom, a nitrogen atom, a sulfur atom, and the like) contained in the compound represented by chemical formula (I) may be an isotope atom other than an isotope which is the most abundant in nature. The isotope atom may be a radioactive isotope atom. That is, according to one aspect of the present invention, the compound of chemical formula (I) already defined herein and labeled with the isotope atom or the salt thereof is provided. Here, the labeling with the isotope atom may be, for example, labeling with a radioactive isotope ($^3$H, $^{14}$C, $^{32}$P, or the like), and is preferably labeling with $^3$H from the aspect of the ease of the preparation of the compound.

In one aspect of the present invention, the compound of chemical formula (I), an enantiomer thereof, a diastereomer thereof, or a pharmaceutically acceptable salt thereof is administered as a prodrug, and is converted into an active compound in the living body.

The pharmaceutical composition of the present invention can be prepared as various dosage forms, for example, for oral administration, a tablet, a capsule, a powder, a granule, a pill, a liquid, an emulsion, a suspension, a solution, a spirit, a syrup, an extract, and an elixir; as a parenteral, for example, injections such as a subcutaneous injection, an intravenous injection, an intramuscular injection, and an intraperitoneal injection; endermic administration or a patch, ointment or a lotion; a sublingual agent and a intraoral patch for intraoral administration; and an aerosol for nasal administration. The pharmaceutical composition of the present invention is not limited to these. These preparations can be produced by a known method usually used in a formulation step.

The pharmaceutical composition can contain various components used generally, and can contain, for example, one or more pharmaceutically acceptable excipients, disintegrants, diluents, lubricants, perfuming agents, coloring agents, sweeteners, flavoring agents, suspending agents, wetting agents, emulsifiers, dispersants, adjuvants, antiseptics, buffers, binders, stabilizers, coating agents, and the like. The pharmaceutical composition of the present invention may be a long acting or sustained-release dosage form.

The dose of the pharmaceutical composition of the present invention can be suitably selected depending on the administration route, the somatotype, the age, the physical condition, the degree of the disease, elapsed time after the onset of the disease of the patient or the like, and the pharmaceutical composition of the present invention can contain a therapeutically effective amount and/or a prophylactically effective amount of the compound of the above-mentioned chemical formula (I). In the present invention, the compound of the above-mentioned chemical formula (I) can be used in a dose of generally 1 to 1000 mg/day/adult, for example, 1 to 200 mg/day/adult, specifically 5 to 100 mg/day/adult, and more specifically 10 to 50 mg/day/adult. The administration of the pharmaceutical composition may be a single administration or multiple administrations.

The pharmaceutical composition of the present invention may contain conventionally known components such as a coloring agent, a preservative, a perfume, a flavor, a coating agent, an antioxidant, vitamins, amino acids, peptides, proteins, and minerals (iron, zinc, magnesium, iodine, and the like) if needed. The pharmaceutical composition of the present invention may be prepared in a form suitable for oral administration, for example a form such as various solid preparations such as a granule (including dry syrups), a capsule (soft capsules and hard capsules), a tablet (including chewable agent), a powder (powder medicines), and a pill and a liquid preparation such as a liquid for internal use (including a liquid, suspension, and syrup).

Examples of an additive for formulation include excipients, lubricants, binders, disintegrants, fluidizing agents, dispersants, wetting agents, antiseptics, thickeners, pH adjusters, coloring agents, correctives, surfactants, and solubilizing agents. In the case of the form of a liquid, thickening agents such as pectin, xanthan gum, and guar gum can be blended. A coating agent may be used to prepare a coated tablet, or a pasty glue. Moreover, even in the case of preparation into other forms, conventional methods may be followed.

The treatment method or preventive method of the present invention may be implemented based on the above-mentioned description. The subject receiving the compound of chemical formula (I) or a pharmaceutically acceptable salt thereof is, for example, a mammal, such as human.

EXAMPLES

The present invention will be described in further detail hereinafter by showing the Examples; however, the present invention is not limited to these Examples.

[Example 1] Preparation of 1-(((2S,4S)-4-((benzyloxy)methyl)-2-phenyl-1,3-dioxolan-2-yl)methyl)-1H-benzo[d][1,2,3]triazole (D-532)

[Chemical Formula 3]

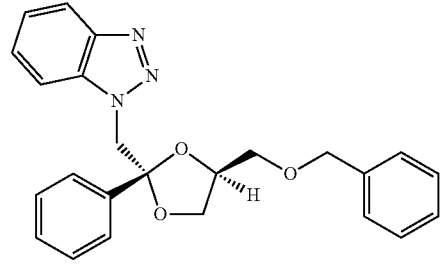

D-532

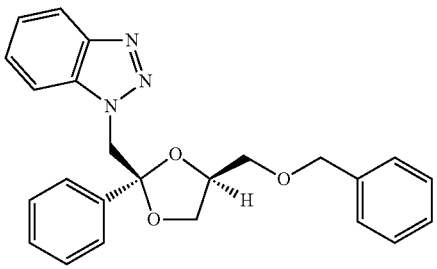

Diastereomer of D-532

To a solution of (R)-(+)-3-benzyloxy-1,2-propanediol (500 mg, 2.74 mmol) and α-(1H-benzotriazol-1-yl)acetophenone (977 mg, 4.12 mmol) in toluene (13.7 mL) was added p-TsOH·H$_2$O (261 mg, 1.37 mmol) at room temperature, and the reaction mixture was stirred under reflux for 18 hours using a dean-stark trap. An aqueous NaHCO$_3$ solution was added at 0° C., the reaction was quenched, and the mixture was extracted with ethyl acetate. The combined organic layer was washed with brine, dried over MgSO$_4$, and concentrated. Purification by column chromatography was performed to obtain a mixture of the title compound (D-532) and a diastereomer thereof (1:1.6) as a yellow oil (234 mg, 0.583 mmol, 21%).

PLC plates of 20×20 cm (silica gel 60 F$_{254}$, 0.5 mm) of Merck KGaA were cut to 10×20 cm, and approximately 10 mg of the diastereomer mixture separated by column chromatography was applied to each cut plate. This was developed with a mixed solvent of ethyl acetate/hexane=½, and the portions corresponding to D-532 and the diastereomer thereof were then shaven off separately, extracted with ethyl acetate to obtain the object and the diastereomer thereof.

D-532: $[\alpha]^{D25}$+14.5 (c 0.466, CHCl$_3$); $^1$H-NMR (700 MHz, CDCl$_3$) δ: 8.04 (dt, J=8.4 Hz, 0.7 Hz, 1H), 7.66 (dt, J=8.4 Hz, 0.7 Hz, 1H), 7.57-7.54 (m, 2H), 7.46 (ddd, J=11.7 Hz, 6.7 Hz, 0.7 Hz, 1H), 7.36-7.33 (m, 4H), 7.28-7.23 (m, 1H), 7.15-7.13 (m, 1H), 4.93 (dd, J=21.7 Hz, 14.7 Hz, 2H), 4.36 (dd, J=11.9 Hz, 7.7 Hz, 2H), 3.81-3.77 (m, 1H), 3.72 (dd, J=8.4 Hz, 7.0 Hz, 1H), 3.52 (dd, J=8.4 Hz, 7.0 Hz, 2H), 3.39 (dd, J=9.8 Hz, 6.0 Hz, 1H), 3.20 (dd, J=10.5 Hz, 8.1 Hz, 1H); $^{13}$C-NMR (175 MHz, CDCl$_3$) δ: 145.7, 140.1, 137.7, 133.9, 128.9, 128.4, 128.3, 127.6, 127.5, 127.3, 125.6, 123.6, 119.6, 76.4, 73.2, 70.1, 68.0, 55.9; MS (EI) calculated for C$_{24}$H$_{23}$N$_3$O$_3$ [M−1]$^+$: 400.1739, found: 400.1686.

Diastereomer of D-532: $[\alpha]^{D25}$+13.9 (c 0.505, CHCl$_3$); $^1$H-NMR (700 MHz, CDCl$_3$) δ: 8.04 (dt, J=8.4 Hz, 0.7 Hz, 1H), 7.69 (dt, J=8.4 Hz, 0.7 Hz, 1H), 7.58-7.56 (m, 2H), 7.46 (ddd, J=7.4 Hz, 4.2 Hz, 0.7 Hz, 1H), 7.39-7.25 (m, 7H), 7.16-7.15 (m, 2H), 4.96 (dd, J=30.5 Hz, 14.7 Hz, 2H), 4.26 (m, 2H), 4.16-4.12 (m, 2H), 3.76 (dd, J=8.4 Hz, 6.3 Hz, 1H), 3.44 (dd, J=8.4 Hz, 4.9 Hz, 1H), 2.89 (dd, J=9.8 Hz, 5.6 Hz, 1H), 2.70 (dd, J=9.8 Hz, 5.6 Hz, 1H); $^{13}$C-NMR (175 MHz, CDCl$_3$) δ: 145.6, 139.2, 137.6, 134.2, 129.1, 128.6, 128.3, 127.69, 127.67, 127.0, 125.9, 123.6, 119.5, 111.1, 109.0, 75.2, 73.3, 70.2, 67.3, 54.9; MS (EI) calculated for C$_{24}$H$_{23}$N$_3$O$_3$ [M]$^+$: 401.1739, found: 401.1731.

The following compounds were prepared by the same technique as in Example 1 using the corresponding acetophenone derivative and/or 1,2-propanediol derivative as a starting material.

[Example 2] Preparation of 1-(((4S)-4-((benzyloxy)methyl)-2-phenyl-1,3-dioxolan-2-yl)methyl)-1H-1,2,4-triazole (D-531)

[Chemical Formula 1]

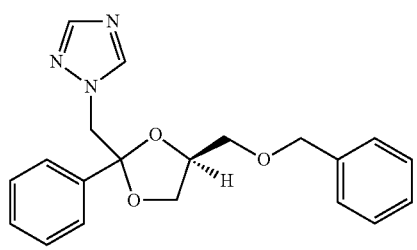

D-531

D-531 (mixture, ~2:1): IR (neat): 3062, 2954, 2897, 1720, 1602, 1584, 1506, 1450, 1365, 1315 cm$^{-1}$; $^1$H-NMR (400 MHz, CDCl$_3$) δ: 8.15 (s, 1H, major), 8.13 (s, 1H, minor), 7.93 (s, 1H, major), 7.90 (s, 1H, minor), 7.70-7.68 (m, 2H), 7.52-7.46 (m, 4H), 7.33-7.24 (m, 8H), 7.17 (d, J=6.8 Hz, 1H), 4.49 (s, 2H, major), 4.45 (s, 2H, minor), 4.30-4.28 (m, 1H), 4.21-4.15 (m, 2H), 4.06-3.98 (m, 1H), 3.92 (t, J=8.2 Hz, 1H, minor), 3.73 (t, J=8.2 Hz, 1H, major), 3.55 (t, J=8.2 Hz, 1H, minor), 3.41 (dd, J=10.1 Hz, 5.8 Hz, 1H, minor), 3.23 (dd, J=9.9 Hz, 5.8 Hz, 1H, minor); $^{13}$C-NMR (100 MHz, CDCl$_3$) δ: 166.0, 15.3, 151.2, 144.5, 139.8, 139.5, 133.0, 129.3, 129.0, 128.9, 128.5, 128.4, 128.3, 128.2, 127.7, 127.5, 125.5, 108.5, 108.1, 96.1, 84.3, 76.6, 75.7, 73.3, 70.2, 67.9, 67.0, 63.2, 60.4, 56.8; MS (FAB) calculated for C$_{20}$H$_{22}$N$_3$O$_3$ [M+H]$^+$: 352.1583, found: 352.1643.

[Example 3] Preparation of 1-(((2S,4S)-4-((benzyloxy)methyl)-2-(4-chlorophenyl)-1,3-dioxolan-2-yl)methyl)-1H-1,2,4-triazole (D-546)

[Chemical Formula 5]

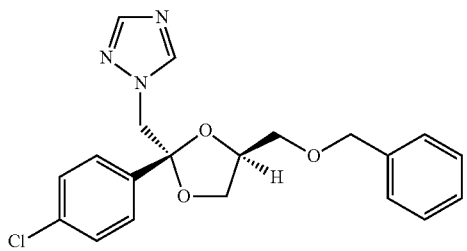

D-546

D-546: $[\alpha]^{D24}$+10.6 (c 0.292, CHCl$_3$); IR (neat): 2865, 2359, 1717, 1598, 1506, 1491, 1453, 1399, 1356 cm$^{-1}$; $^1$H-NMR (400 MHz, CDCl$_3$) δ: 8.13 (s, 1H), 7.90 (s, 1H), 7.40 (d, J=8.8 Hz, 2H), 7.31-7.27 (m, 4H), 7.17 (d, J=7.8 Hz, 1H), 4.46 (s, 2H), 4.41 (s, 2H), 4.07 (quin, J=5.9 Hz, 1H), 3.94 (dd, J=8.3 Hz, 6.3 Hz, 1H), 3.58 (t, J=8.3 Hz, 1H), 3.40 (dd, J=10.2 Hz, 5.6 Hz, 1H), 3.26 (dd, J=10.2 Hz, 5.4 Hz, 1H); $^{13}$C-NMR (100 MHz, CDCl$_3$) δ: 151.4, 144.5, 138.4, 137.5, 135.0, 128.7, 128.4, 127.8, 127.6, 127.1, 107.8, 76.8, 73.4, 69.9, 67.9, 56.7; MS (FAB) calculated for C$_{20}$H$_{21}$ClN$_3$O$_3$ [M+H]$^+$: 386.1193, found: 386.1261.

[Example 4] Preparation of 1-(((2S,4S)-4-((benzyloxy)methyl)-2-(2,4-dichlorophenyl)-1,3-dioxolan-2-yl)methyl)-1H-1,2,4-triazole (D-547)

[Chemical Formula 6]

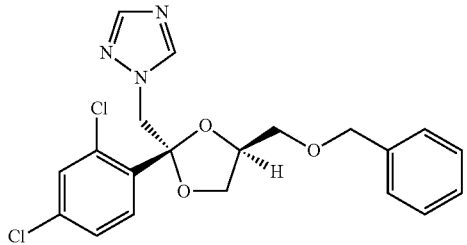

D-547

D-547: $[\alpha]^{D26}$+7.23 (c 0.493, CHCl$_3$); IR (neat): 2865, 1718, 1586, 1557, 1506, 1453, 1378, 1314 cm$^{-1}$; $^1$H-NMR (400 MHz, CDCl$_3$) δ: 8.16 (s, 1H), 7.89 (s, 1H), 7.52 (d, J=8.8 Hz, 1H), 7.41 (d, J=2.0 Hz, 1H), 7.32-7.25 (m, 3H), 7.16-7.13 (m, 3H), 4.72 (dd, J=16.8 Hz, 15.1 Hz, 2H), 4.41 (s, 2H), 4.08-4.02 (m, 1H), 3.95 (dd, J=8.3 Hz, 5.9 Hz, 1H), 3.65 (t, J=8.3 Hz, 1H), 3.43 (dd, J=10.2 Hz, 4.9 Hz, 1H), 3.34 (dd, J=10.2 Hz, 5.4 Hz, 1H); $^{13}$C-NMR (100 MHz, CDCl$_3$) δ: 137.5, 135.7, 15.2, 132.9, 131.1, 129.4, 128.4, 128.3, 127.8, 127.5, 127.1, 107.6, 76.8, 69.4, 67.6, 54.4; MS (FAB) calculated for C$_{20}$H$_{20}$Cl$_2$N$_3$O$_3$ [M+H]$^+$: 420.0803, found: 420.0860.

[Example 5] Preparation of 1-(((2R,4S)-4-((benzyloxy)methyl)-2-(4-chlorophenyl)-1,3-dioxolan-2-yl)methyl)-1H-1,2,4-triazole (D-548)

[Chemical Formula 7]

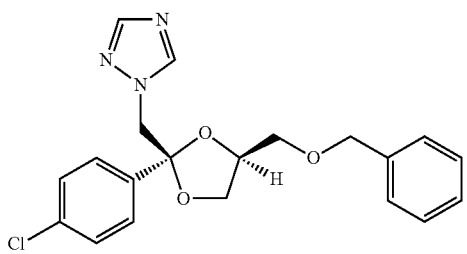

D-548

D-548: IR (neat): 3031, 2889, 1722, 1598, 1506, 1491, 1453, 1420, 1399, 1365 cm$^{-1}$; $^1$H-NMR (400 MHz, CDCl$_3$) δ: 8.15 (s, 1H), 7.88 (s, 1H), 7.43-7.24 (m, 7H), 7.17 (d, J=10.6 Hz, 2H), 4.49 (d, J=10.1 Hz, 2H), 4.46 (d, J=13.5 Hz, 2H), 4.18 (quin, J=5.8 Hz, 1H), 3.81 (t, J=8.2 Hz, 1H), 3.64 (dd, J=8.7 Hz, 5.3 Hz, 1H), 3.27 (dd, J=9.7 Hz, 5.8 Hz, 1H), 3.11 (dd, J=9.7 Hz, 5.8 Hz, 1H); $^{13}$C-NMR (100 MHz, CDCl$_3$) δ: 151.2, 144.7, 137.6, 137.5, 135.2, 128.8, 128.5, 127.9, 127.8, 127.3, 107.7, 77.2, 75.3, 73.5, 70.0, 67.4, 55.9; MS (EI) calculated for C$_{20}$H$_{20}$ClN$_3$O$_3$ [M]$^+$: 385.1193, found: 385.1187.

[Example 6] Preparation of 1-(((2S,4S)-4-((benzyloxy)methyl)-2-(4-chlorophenyl)-1,3-dioxolan-2-yl)methyl)-1H-imidazole (D-552)

[Chemical Formula 8]

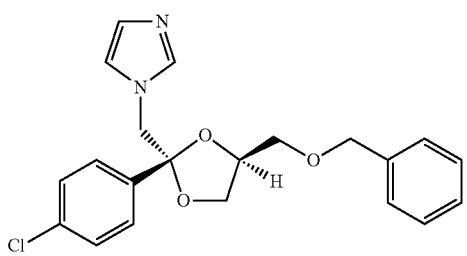

D-552

D-552: IR (neat): 3031, 2865, 1721, 1599, 1505, 1491, 1453, 1399 cm$^{-1}$; $^1$H-NMR (400 MHz, CDCl$_3$) δ: 7.41-7.20 (m, 8H), 7.13 (d, J=7.8 Hz, 2H), 6.96 (s, 1H), 6.90 (s, 1H), 4.37 (s, 2H), 4.06 (s, 2H), 3.98 (quin, J=5.9 Hz, 1H), 3.80 (dd, J=8.0 Hz, 6.3 Hz, 1H), 3.49 (t, J=7.3 Hz, 1H), 3.31 (dd, J=10.2 Hz, 5.9 Hz, 1H), 3.21 (dd, J=10.2 Hz, 5.4 Hz, 1H); $^{13}$C-NMR (100 MHz, CDCl$_3$) δ: 138.9, 138.6, 137.5, 134.8, 133.2, 129.5, 128.7, 128.5, 128.4, 128.3, 127.8, 127.6, 127.0, 120.1, 108.0, 76.8, 73.3, 69.9, 67.8, 54.7; MS (FAB) calculated for C$_{21}$H$_{22}$ClN$_2$O$_3$ [M+H]$^+$: 385.1241, found: 385.1313.

[Example 7] Preparation of 1-(((2S,4S)-4-((benzyloxy)methyl)-2-(2,4-dichlorophenyl)-1,3-dioxolan-2-yl)methyl)-1H-imidazole (D-555)

[Chemical Formula 9]

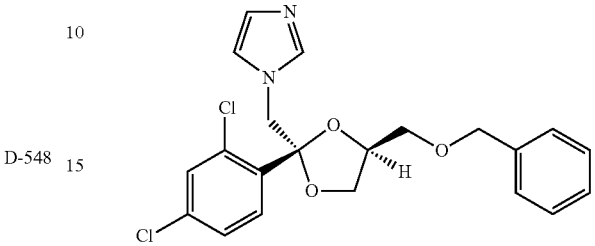

D-555

D-555: IR (neat): 3064, 3030, 2897, 1721, 1586, 1557, 1505, 1466, 1435, 1377, 1313 cm$^{-1}$; $^1$H-NMR (400 MHz, CDCl$_3$) δ: 7.57-7.53 (m, 2H), 7.40 (d, J=1.9 Hz, 1H), 7.33-7.27 (m, 3H), 7.17-7.13 (m, 3H), 7.01 (s, 1H), 6.97 (s, 1H), 4.41 (s, 2H), 4.39 (d, J=3.9 Hz, 2H), 3.99 (quin, J=5.8 Hz, 1H), 3.83 (dd, J=8.0 Hz, 6.3 Hz, 1H), 3.59 (t, J=7.7 Hz, 1H), 3.39 (dd, J=10.1 Hz, 5.3 Hz, 1H), 3.31 (dd, J=10.4 Hz, 4.8 Hz, 1H); $^{13}$C-NMR (100 MHz, CDCl$_3$) δ: 138.7, 137.6, 135.6, 135.5, 132.7, 131.0, 129.4, 129.3, 128.5, 128.34, 128.27, 127.7, 127.5, 127.0, 120.9, 107.9, 76.8, 73.4, 69.4, 67.6, 52.2; MS (FAB) calculated for C$_{21}$H$_{21}$Cl$_2$N$_2$O$_3$ [M+H]$^+$: 419.0851, found: 419.0913.

[Example 8] Preparation of 1-(((4S)-4-((benzyloxy)methyl)-2-phenyl-1,3-dioxolan-2-yl)methyl)-1H-imidazole (D-557)

[Chemical Formula 10]

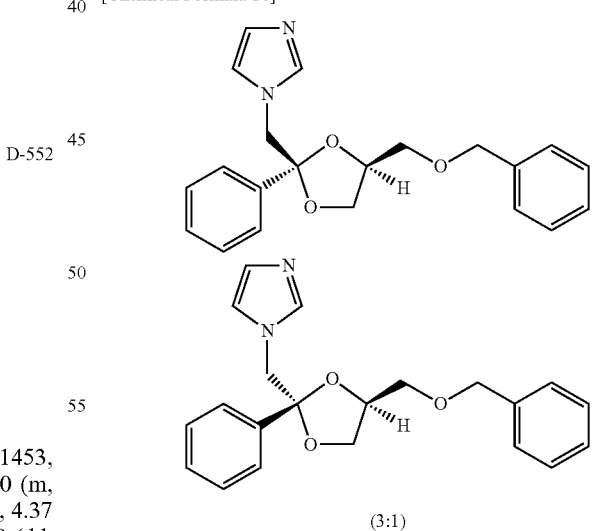

(3:1)

D-557 (mixture, ~3:1): IR (neat): 3061, 3030, 2887, 1721, 1602, 1505, 1449, 1386, 1314 cm$^{-1}$; $^1$H-NMR (400 MHz, CDCl$_3$) δ: 7.45-7.43 (m, 4H), 7.34-7.23 (m, 7H), 6.94 (s, 1H), 6.91 (s, 1H), 4.49 (d, J=12.1 Hz, 1H), 4.41 (d, J=12.1 Hz, 1H), 4.17-4.13 (m, 3H), 3.77 (t, J=7.7 Hz, 1H), 3.49 (dd, J=8.2 Hz, 5.3 Hz, 1H), 3.20 (dd, J=9.7 Hz, 6.3 Hz, 1H), 3.03

(dd, J=9.9 Hz, 5.8 Hz, 1H); $^{13}$C-NMR (100 MHz, CDCl$_3$) δ: 139.5, 138.8, 137.7, 133.3, 129.7, 129.0, 128.9, 128.54, 128.47, 128.44, 128.41, 128.3, 127.83, 127.78, 125.71, 125.68, 121.1, 108.3, 75.3, 74.2, 73.4, 70.4, 67.4, 67.1, 64.2, 53.9; MS (EI) calculated for C$_{21}$H$_{22}$N$_2$O$_3$ [M]$^+$: 350.1630, found: 350.1651.

[Example 9] Preparation of 1-(((4S)-4-((benzoyloxy)methyl)-2-(2,4-dichlorophenyl)-1,3-dioxolan-2-yl)methyl)-1H-1,2,4-triazole (D-535)

[Chemical Formula 11]

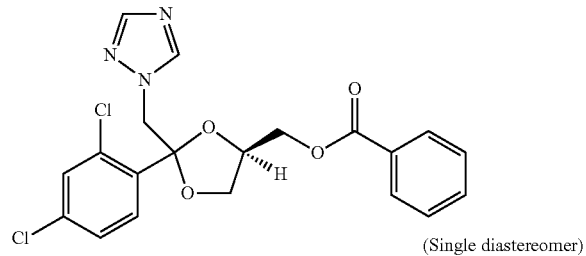

D-535

(Single diastereomer)

D-535: [α]$^{D26}$+14.5 (c 0.303, CHCl$_3$); IR (neat): 2919, 1721, 1586, 1557, 1506, 1466, 1451, 1378, 1315 cm$^{-1}$; $^1$H-NMR (400 MHz, CDCl$_3$) δ: 8.18 (s, 1H), 7.91 (s, 1H), 7.69 (dd, J=8.5 Hz, 0.98 Hz, 2H), 7.56-7.52 (m, 2H), 7.37-7.33 (m, 2H), 7.12 (dd, J=8.5 Hz, 2.0 Hz, 1H), 4.73 (s, 2H), 4.46 (dd, J=11.2, 3.4 Hz, 1H), 4.22-4.16 (m, 2H), 4.04-4.01 (m, 1H); $^{13}$C-NMR (100 MHz, CDCl$_3$) δ: 200.2, 165.9, 15.6, 135.8, 134.8, 133.3, 133.1, 131.2, 129.4, 129.1, 128.3, 127.2, 108.0, 75.9, 66.8, 62.4, 54.4, 52.1; MS (FAB) calculated for C$_{20}$H$_{18}$Cl$_2$N$_3$O$_4$ [M+H]$^+$: 434.0596, found: 434.0673.

[Example 10] Preparation of 1-(((2R,4S)-4-((benzyloxy)methyl)-2-(4-chlorophenyl)-1,3-dioxolan-2-yl)methyl)-1H-imidazole (D-534)

[Chemical Formula 12]

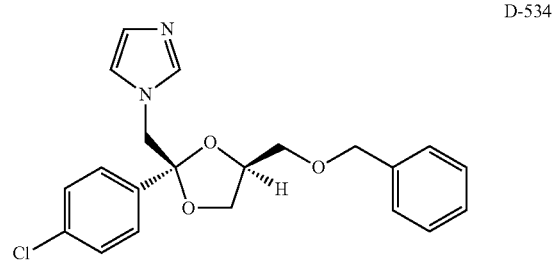

D-534

D-534: IR (neat): 3031, 2886, 1721, 1598, 1505, 1490, 1453, 1434, 1399 cm$^{-1}$; $^1$H-NMR (400 MHz, CDCl$_3$) δ: 7.44 (s, 1H), 7.40-7.26 (m, 9H), 6.98 (s, 1H), 6.91 (s, 1H), 4.52 (d, J=12.2 Hz, 1H), 4.44 (d, J=12.2 Hz, 1H), 4.20-4.13 (m, 3H), 3.54 (dd, J=7.8, 6.8 Hz, 1H), 3.54 (dd, J=8.3, 5.4 Hz, 1H), 3.24 (dd, J=10.0, 6.3 Hz, 1H), 3.09 (dd, J=9.8 Hz, 5.4 Hz, 1H); $^{13}$C-NMR (100 MHz, CDCl$_3$) δ: 138.7, 138.0, 137.7, 137.0, 135.0, 129.7, 128.8, 128.7, 128.5, 128.42, 128.36, 127.8, 127.2, 121.0, 77.2, 76.7, 75.4, 74.3, 73.4, 70.2, 67.4, 53.8; MS (EI) calculated for C$_{21}$H$_{21}$ClN$_2$O$_3$ [M]$^+$: 384.1241, found: 384.1242.

[Test Example 1] Production of a SV40MES13-ChoRE-Luc_FLAG-ChREBP Cells

The following cells were produced to perform assay as to the expression of carbohydrate-responsive element-binding protein (abbreviated name: ChREBP).

An ACC ChoRE/PK-luc reporter plasmid (Stoeckman et al (2004) J Biol Chem 15, 15662-15669) was obtained from Dr. Howard C. Towle at the University of Minnesota. The insertion of the above-mentioned plasmid was subcloned according to the protocol attached to the pGL4.15 vector (Promega Corporation). The obtained expression vector was introduced into SV40 MES13 cells (ATCC Corporation) according to the protocol attached to pGL4.15 vector to obtain SV40MES13-ChoRE-Luc cells.

Moreover, pQCXIH FLAG ChREBP was further introduced into the SV40MES13-ChoRE-Luc cells in expectation of the sensitization of reporter assay using the SV40MES13-ChoRE-Luc cells to obtain the cell line: SV40MES13-ChoRE-Luc_FLAG-ChREBP for reporter assay.

pQCXIH FLAG ChREBP was obtained as follows. mRNA was first extracted from pieces of the mouse liver using TRIzol Reagent (Thermo Fisher Scientific K.K.) according to the protocol attached to the kit, and the obtained mRNA was subjected to cDNA library preparation according to the protocol attached to the Superscript III reverse transcriptase (Thermo Fisher Scientific K.K.). cDNA encoding ChREBP was obtained as an amplified fragment using this as a template and using the following primer set.

```
Forward:
5'-ATGCATCTCGAGATGGCGCGCGCGCTGGCGGATCTA-3',

Reverse:
5'-ATGCATGCGGCCGCTTATAATGGTCTCCCCAGGGTGCC-3'.
```

The amplified fragment was subcloned according to the protocol attached to the pQCXIH-FLAG vector (Clontech Laboratories, Inc.).

FIG. 1 shows the results of the Western blotting analysis of proteins derived from the cells SV40MES13, SV40MES13-ChoRE-Luc, and SV40MES13-ChoRE-Luc FLAG-ChREBP. In the SV40MES13-ChoRE-Luc_FLAG-ChREBP cells, anti-FLAG antibody (Merck KGaA)- and anti-ChREBP antibody (Novus Biologicals, LLC)-positive bands were confirmed, and the expression of ChREBP protein derived from pQCXIH FLAG ChREBP was confirmed.

Figure 2:
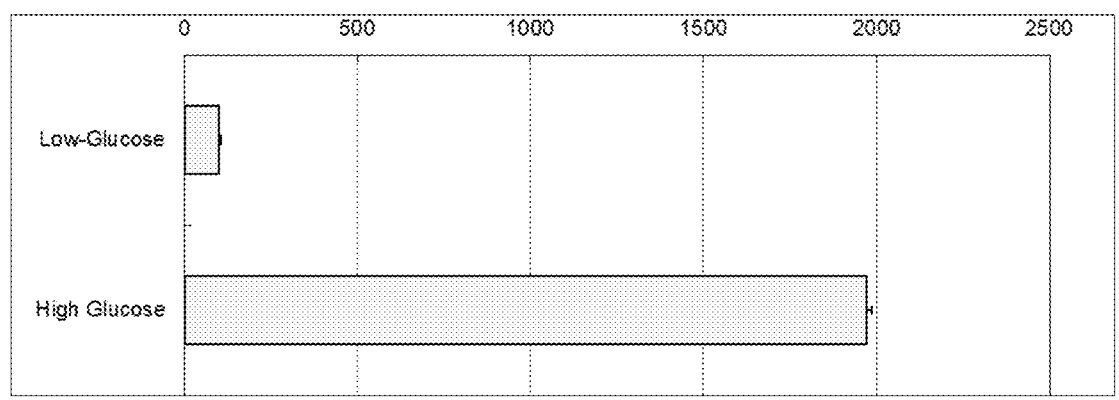
FIG. 2 is a graph showing luciferase activity when SV40MES13-ChoRE-Luc_FLAG-ChREBP cells were cultured in low glucose (5.5 mM) or high glucose (25 mM) DMEM medium.
Figure 3:
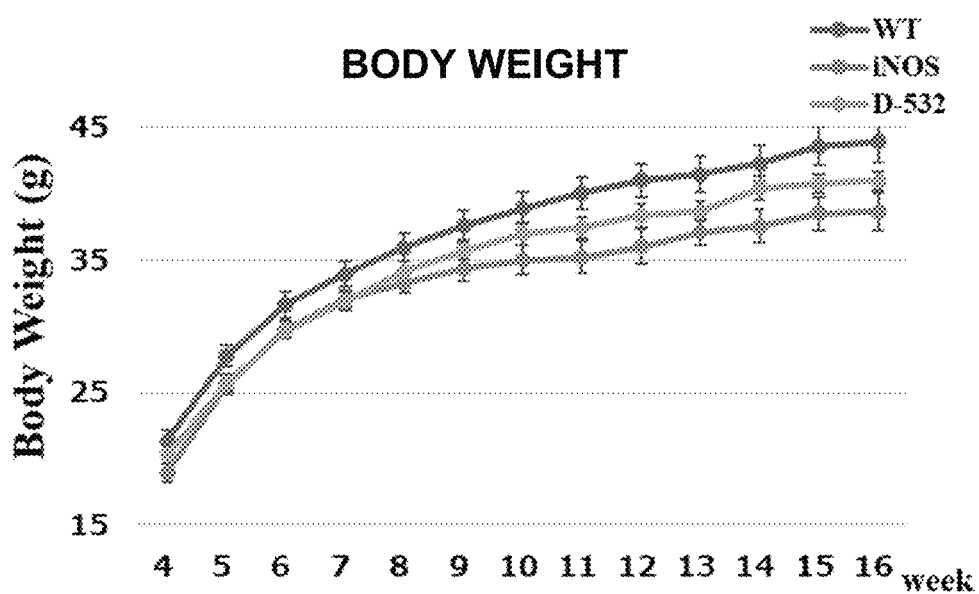
FIG. 3 is a graph showing the transition of the average weights of mice in groups.

When the luciferase activity at the time of culturing the SV40MES13-ChoRE-Luc FLAG-ChREBP cells in low glucose (5.5 mM) or high glucose (25 mM) DMEM medium was measured according to a previous report (Biochemical and Biophysical Research Communications 489 (2017) 21-28), a remarkable difference in activity between the two groups was confirmed. FIG. 2 shows the results.

[Test Example 2] Assay Using SV40MES13-ChoRE-Luc_FLAG-ChREBP Cells

Figure 12:
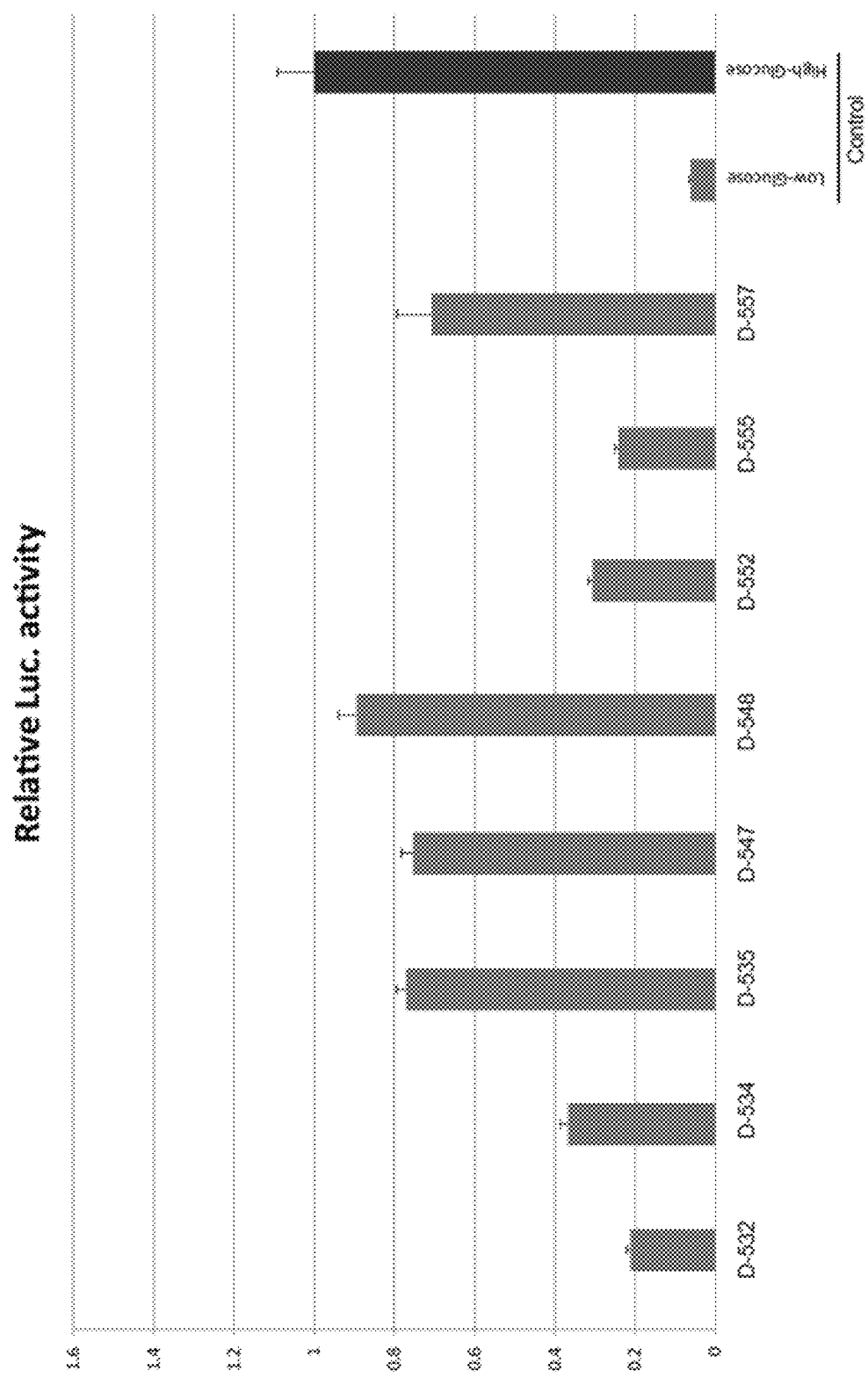
FIG. 12 is a graph showing the test results for confirming the effect of a compound according to the present invention on the expression amounts of carbohydrate-responsive element-binding protein (ChREBP).
Figure 13:
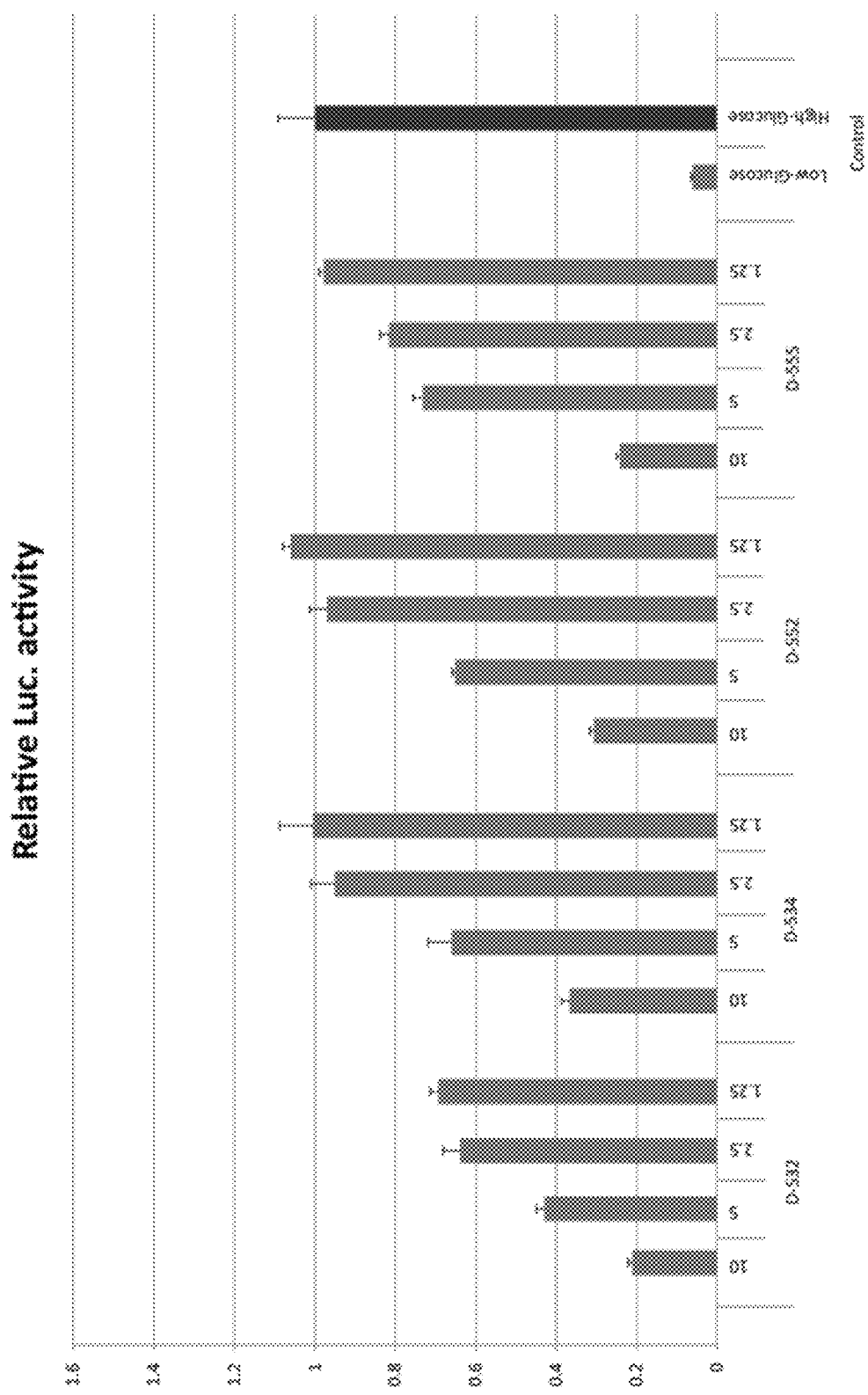
FIG. 13 is a graph showing the test results for confirming the effect of a compound according to the present invention on the expression amounts of carbohydrate-responsive element-binding protein (ChREBP) (the concentrations are shown in terms of μM).

First, 10$^4$ SV40MES13-ChoRE-Luc_FLAG-ChREBP cells were subjected to plating per well of a Corning 384-well plate (Corning, Inc.) and cultured in DMEM medium for 1 day. On the next day, the medium was exchanged for high glucose (25 mM) DMEM medium. To this was added one compound so that the concentration was 20 µM, and culture was performed for 1 day. Then, the luciferase activity of each well was measured. FIG. 12 shows the results. It was confirmed that the test compounds suppress the expression of ChREBP in the cells cultured using the high glucose medium. FIG. 13 shows the results after tests as to compounds at a plurality of concentrations (the concentration is shown in terms of µM).

[Test Example 3] Test Using Mice Developing Diabetic Nephropathy iNOS transgenic mice (Takamura T. et al., J Biol Chem. 1998; 273: 2493-2496; received from Emeritus Professor Hiroshi Okamoto, Tohoku University) were used as model mice. According to the literature of Takamura et al., breeding in which 4-week-old model mice (experimental group: n=8, control group: n=6) and a wild type group (n=8), which is non-transgenic mice born simultaneously with the model mice by mating iNOS transgenic mice and wild type (CD1 (ICR)) mice, were fed with high protein and high calorie diets was performed for 13 weeks. Compound 12 (D-532) was further orally administered to the experimental group in 6 mg/kg/day. As to the groups, the body weights were measured every day, and the blood sugar levels, the albumin in urine, and the creatinine in urine were measured in accordance with the usual method every 3 weeks. The groups were sacrificed after the breeding, the serum creatinine in the blood collected from the abdominal vena cava at the time of dissection was measured, and the gene expression in the kidneys collected at the time of dissection was analyzed. The kidney tissues were stained with HE and PAS and observed.

Figure 4:
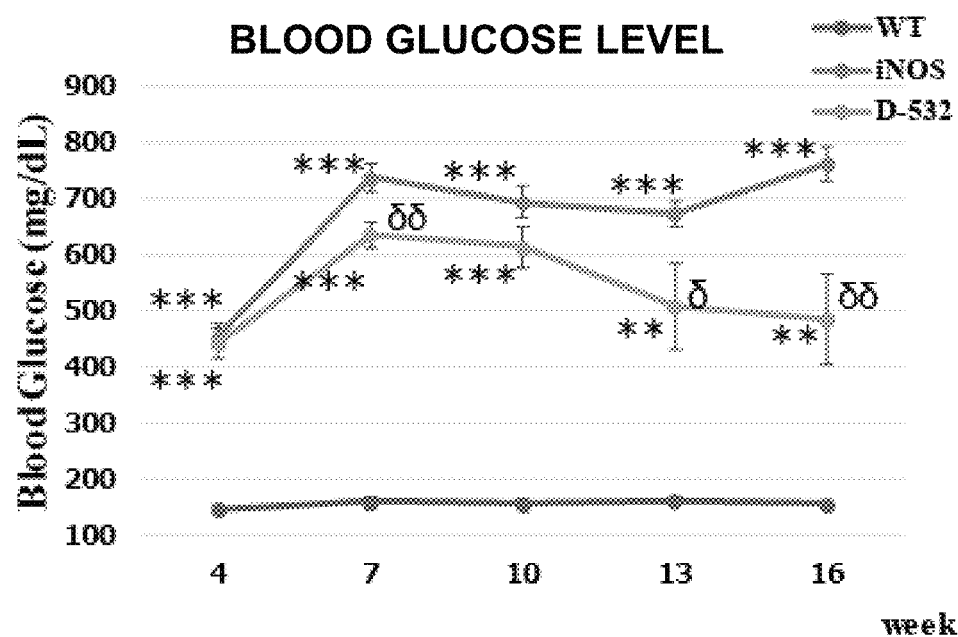
FIG. 4 is a graph showing the transition of the blood sugar levels of mice in groups (average values). With respect to a WT mouse group, it is meant that : $p<0.01$ and *: $p<0.001$. With respect to a non-administered group of iNOS mice, it is meant that δ: $p<0.05$ and δδ: $p<0.01$. Herein, it is meant that *: $p<0.05$, : $p<0.01$, *: $p<0.001$, δ: $p<0.05$, δδ: $p<0.01$, and δδδ: $p<0.001$ (in the other figures, the same are also meant).
Figure 5:
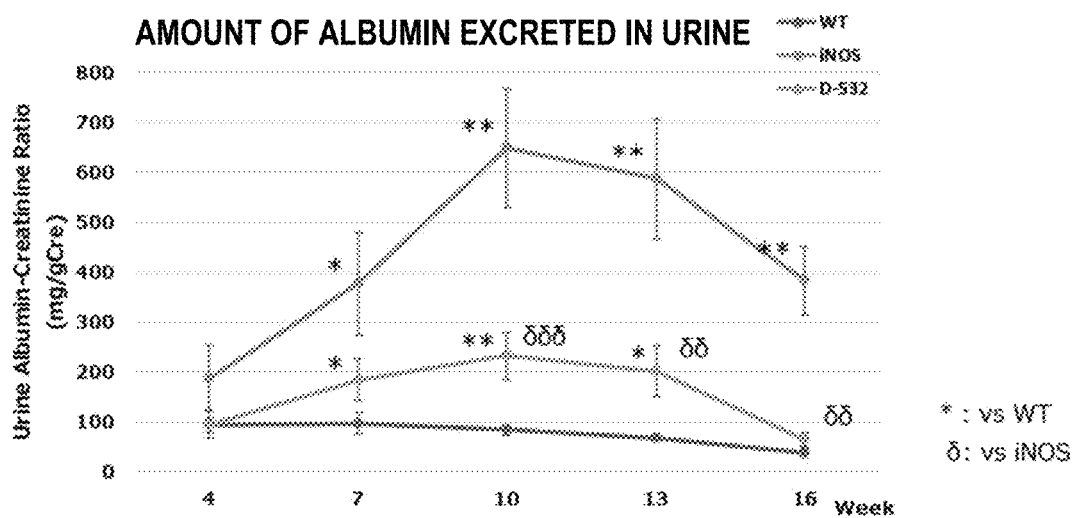
FIG. 5 is a graph showing the transition of the amounts of albumin excreted in urine of mice in groups (average values). With respect to a WT mouse group, it is meant that *: $p<0.05$, **: $p<0.01$. With respect to a non-administered group of iNOS mice, it is meant that δδ: $p<0.01$, and δδδ: $p<0.001$.
Figure 6:
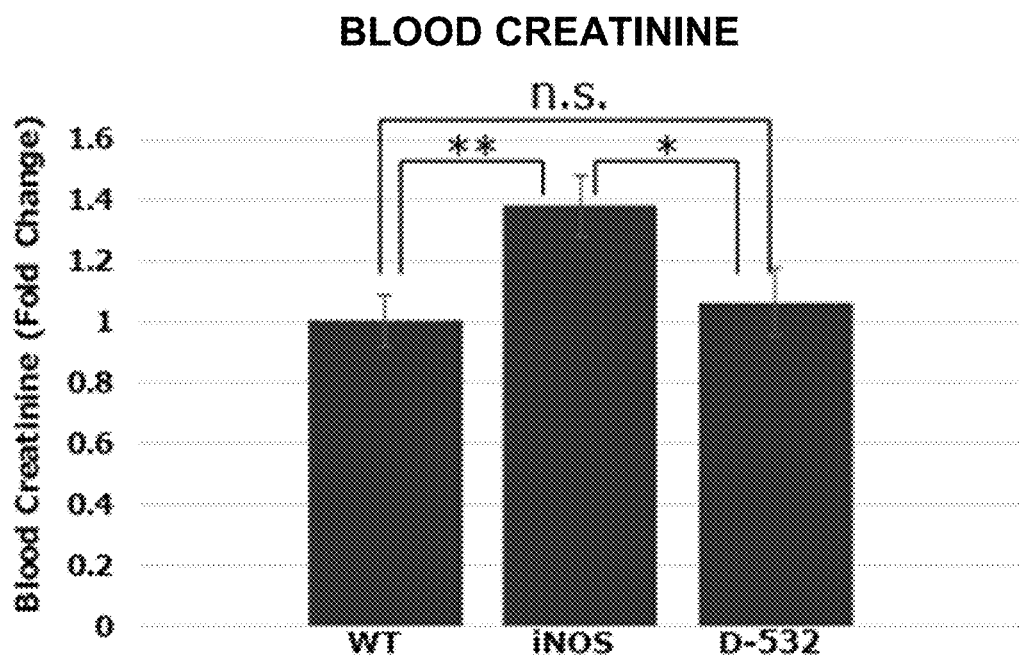
FIG. 6 is a graph showing the measurement results of the blood creatinine levels measured at the time of mouse dissection. It is meant that : $p<0.01$ and *: $p<0.001$.
Figure 7:
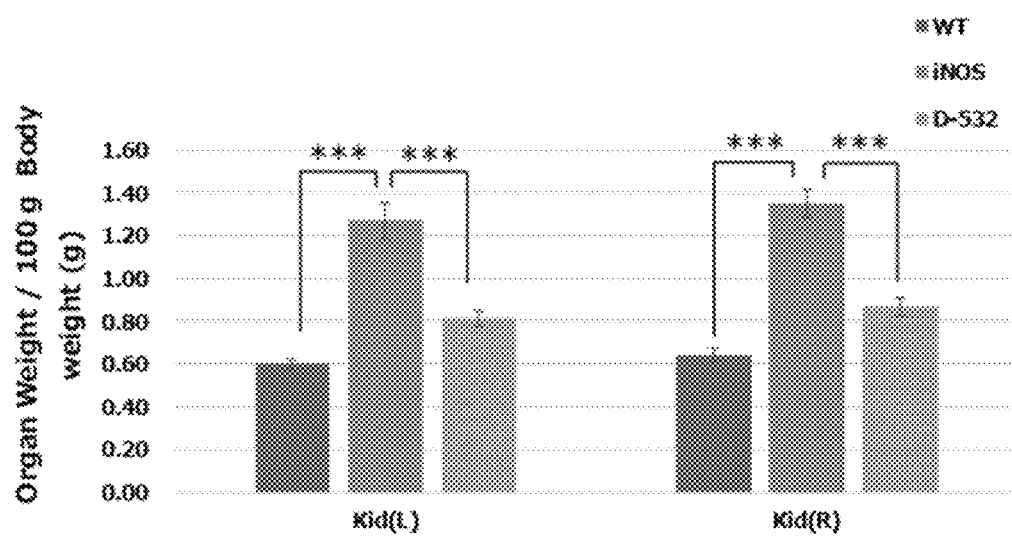
FIG. 7 is a graph showing the measurement results of the kidney weights measured at the time of mouse dissection. It is meant that ***: $p<0.001$.
Figure 8:
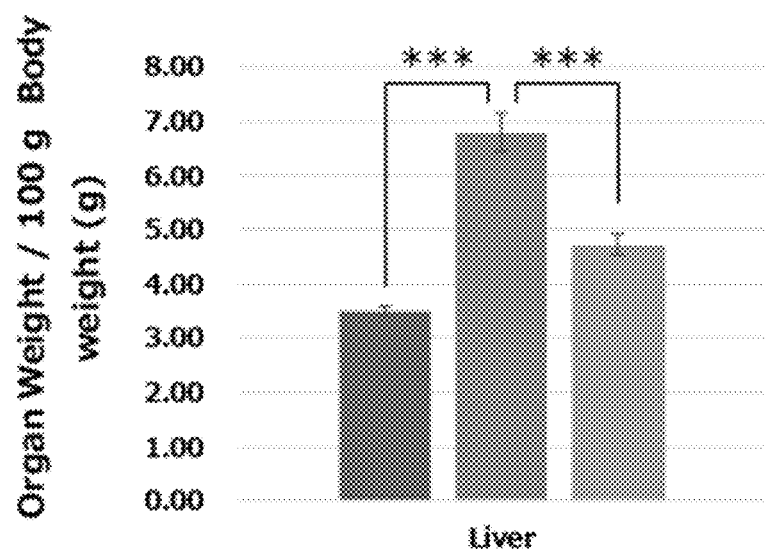
FIG. 8 is a graph showing the measurement results of the liver weights measured at the time of mouse dissection. It is meant that ***: $p<0.001$.
Figure 9:
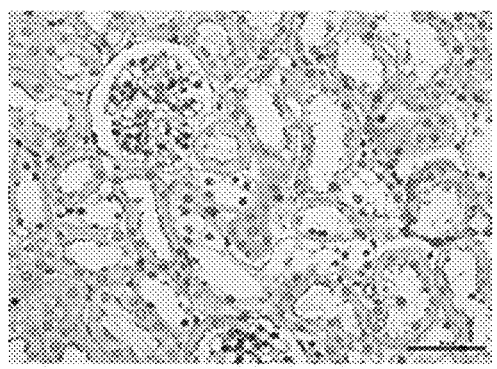
FIG. 9 is photomicrographs of kidney tissues stained with PAS and a graph showing the PAS-positive area ratios in glomeruli. It is meant that ***: $p<0.001$.
Figure 9:
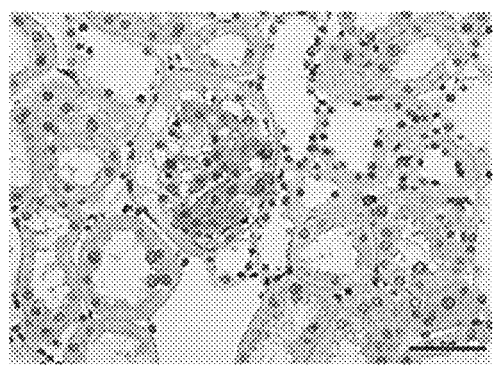
Figure 9:
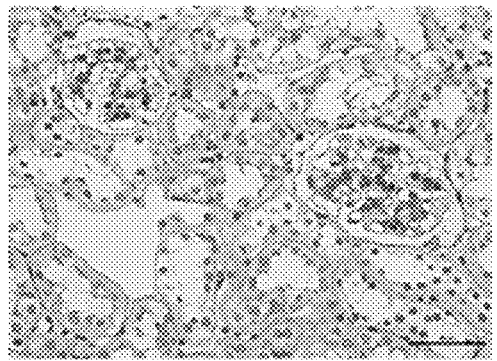
Figure 9:
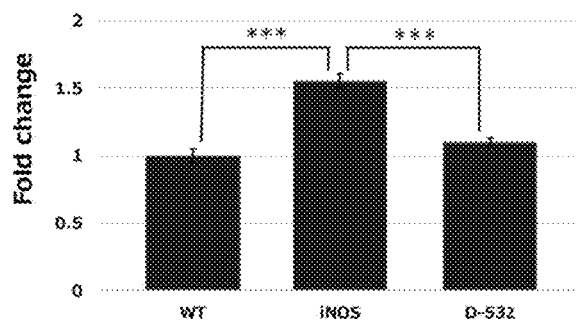

In the compound 12 (D-532)-administered group, the blood sugar level exhibited a significantly low value as compared with the control group (FIG. 4). The amount of albumin excreted in urine also exhibited a significant low value in the compound 12 (D-532)-administered group as compared with the control group (FIG. 5), and increase in blood creatinine in the model mice was significantly improved by the administration of the compound (FIG. 6). As to both FIG. 4 and FIG. 5, * and δ show the results of significant difference tests (Student's T-tests) with respect to the wild type mice (WT) and with respect to the positive control mice (iNOS), respectively [*: $p<0.05$, : $p<0.01$, *: $p<0.001$ (with respect to δ, the same are also meant)].

Although increase in the weights of the livers and the kidneys was confirmed in the model mice, it was significantly improved in the compound-administered group. Further, the PSA-stained tissue section images were subjected to ImageJ (http://imagej.nih.gov/ij/) and measured according to the operation manual attached to ImageJ. When each glomerulus area (each group, n=100) and an area obtained by excluding regions of no interest such as vascular lumens and nuclei from the each glomerulus area were found, and the ratio therebetween, namely the PAS-positive area ratio in glomeruli, was found, the ratio increased in the model mice, and the improvement was meanwhile confirmed in the administered group.

[Test Example 4] ChREBP Target Gene Expression Analysis

In the mice used in Test Example 3, the expression variations of ChREBPβ and the TXNIP genes, which are target genes of ChREBP in the kidney, were analyzed by quantitative PCR in the method of the previous report (Genes to Cells 19 (2013) 52-65). The following primer set was used for the amplification of ChREBPβ.

```
Forward:    5'-TCTGCAGATCGCGTGGAG-3'
Reverse:    5'-CTTGTCCCGGCATAGCAAC-3'
```

A primer set used for the amplification of the TXNIP gene is as mentioned above.

```
Forward:    5'-GTCAGTGTCCCTGGCTCCAAGA-3'
Reverse:    5'-AGCTCATCTCAGAGCTCGTCCG-3'
```

Figure 10:
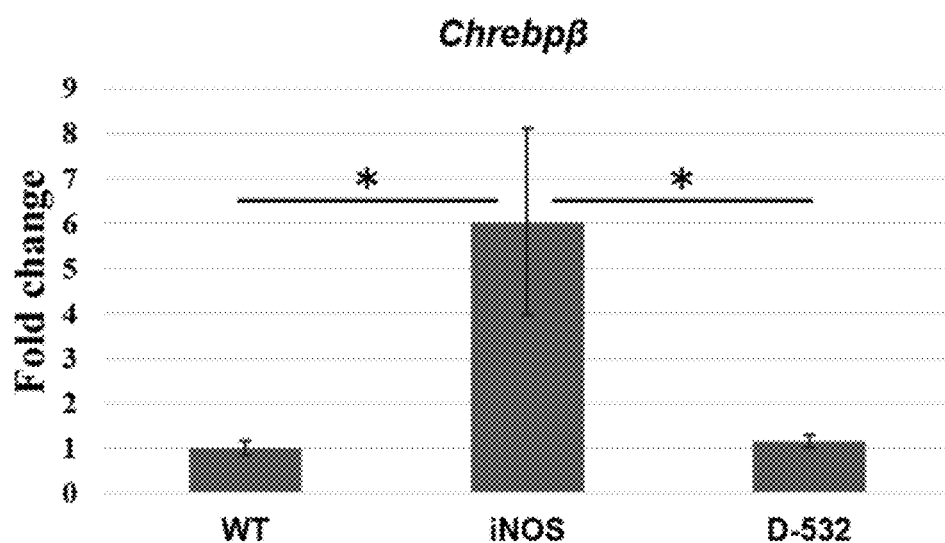
FIG. 10 is a graph showing the results obtained by analyzing the expression variations of the ChREBPβ gene, which is a target gene of ChREBP, in the kidney by quantitative PCR. It is meant that *: $p<0.05$.
Figure 11:
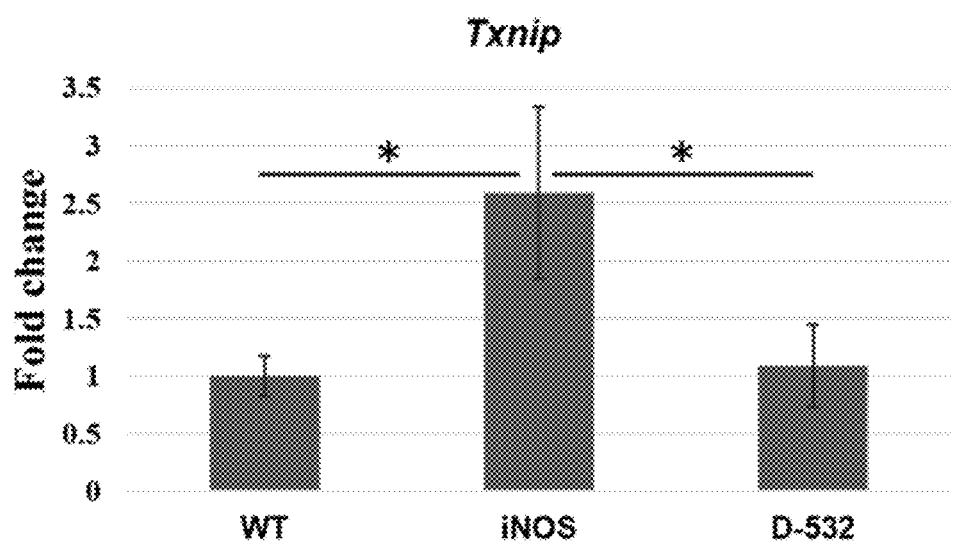
FIG. 11 is a graph showing the results obtained by analyzing the expression variations of the TXNIP gene, which is a target gene of ChREBP, in the kidney by quantitative PCR. It is meant that *: $p<0.05$.

FIG. 10 and FIG. 11 show the results. As to ChREBPβ and TXNIP, decrease in expression by D532 administration was observed.

[Test Example 5] Cell Survivability Test

Figure 14:
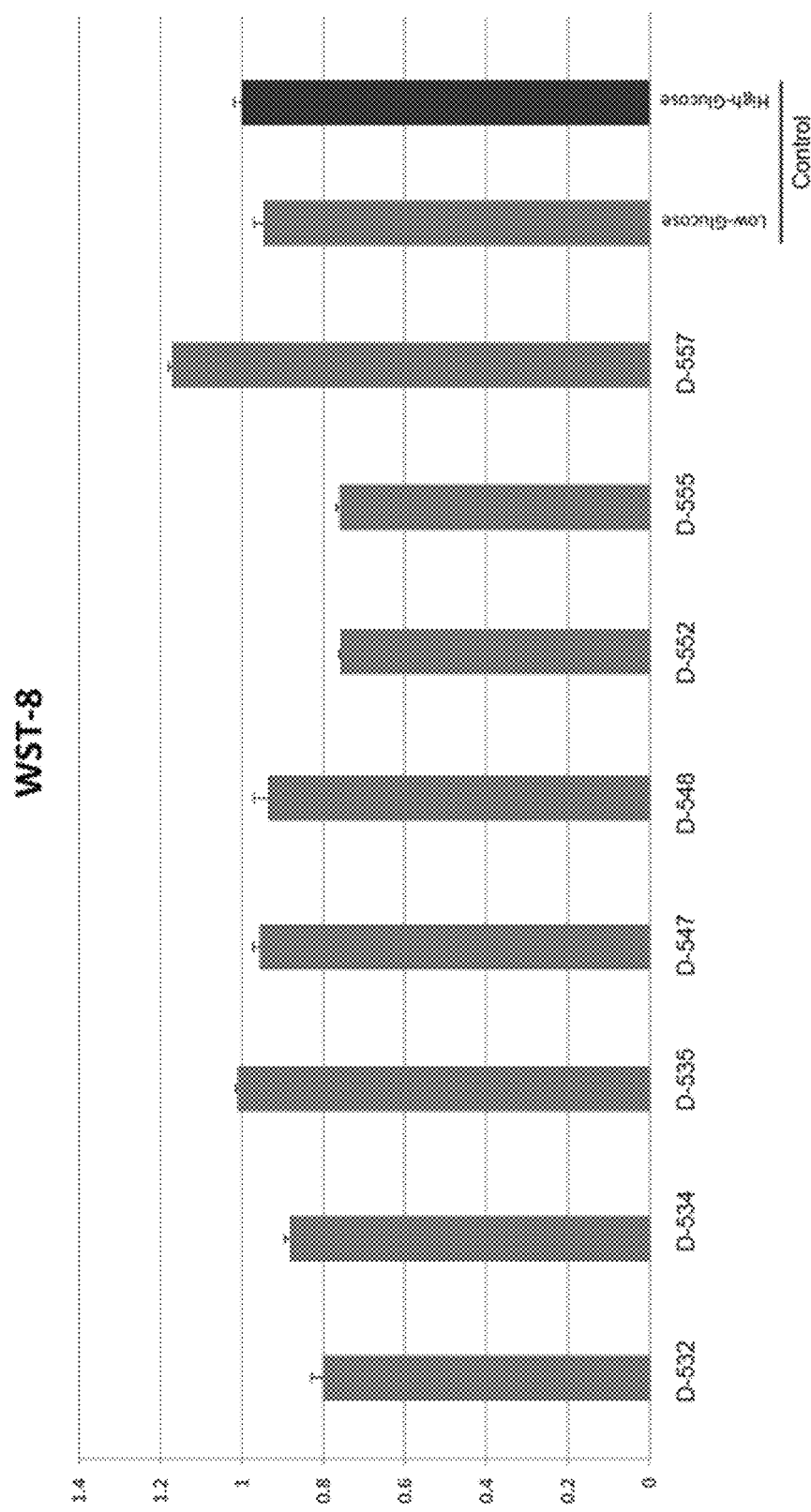
FIG. 14 is a graph showing the test results for confirming influence which a compound according to the present invention has on the cell survivabilities.
Figure 15:
FIG. 15 is a graph showing the test results for confirming influence which a compound according to the present invention has on the cell survivabilities (the concentrations are shown in terms of μM).

Cell survivability tests were performed using SV40MES13-ChoRE-Luc_FLAG-ChREBP cells and using the method for measuring luciferase activity described in the previous report (Biochemical and Biophysical Research Communications 489 (2017) 21-28). SV40MES13-ChoRE-Luc_FLAG-ChREBP cells were cultured in low glucose (5.5 mM) DMEM medium for 24 hours, the medium was then exchanged for high glucose (25 mM) DMEM media containing compounds (the experimental group), low glucose DMEM medium containing no compound and high glucose DMEM medium containing no compound (all corresponding to the control group), and the luciferase activities derived from the cells cultured for 24 hours after the exchange were measured according to the previous report. FIG. 14 shows the results. Moreover, FIG. 15 shows the results after tests as to compounds at a plurality of concentrations (the concentration is shown in terms of µM).

[Test Example 6] Observation of Mouse Kidney Tissues

The kidneys of model mice in the administered group and the non-administered group, and a mouse in the wild type group in Test Example 3 were placed in a prefixing solution containing 2% PFA (FUJIFILM Wako Pure Chemical Corporation; 163-20145)/2.5% glutaraldehyde (TAAB Laboratories Equipment Ltd.; G017/1)/0.1 M cacodylate buffer solution (FUJIFILM Wako Pure Chemical Corporation; 036-18175) and treated at room temperature for 2 hours. The prefixed kidneys were washed with 0.1 M cacodylate buffer solution (containing 8% sucrose (FUJIFILM Wako Pure Chemical Corporation: 196-00015)) on ice for 15 minutes×4 times and treated with postfixing solution containing 1% osmium tetroxide (FUJIFILM Wako Pure Chemical Corporation; 154-01014) on ice for 90 minutes. The postfixed kidneys were washed with ultrapure water for 15 minutes×3 times, placed in aqueous 50, 60, 70, 80, 90, and 95% ethanol solutions each for 10 minutes×1 time, further in 100% ethanol for 20 minutes×3 times, and subjected to ethanol dehydration. After the dehydration, the kidneys were reacted with propylene oxide (FUJIFILM Wako Pure Chemical Corporation; 165-05026) for 10 minutes×2 times, then reacted with a mixed solution of propylene oxide/EPON Resin (MNA (TAAB Laboratories Equipment Ltd.; M012): DDSA (TAAB Laboratories Equipment Ltd.; D027):Epon 812 (TAAB Laboratories Equipment Ltd.; T026):DMP-30 (TAAB Laboratories Equipment Ltd.; D032)=20:10:30:1) (1:1) at room temperature for 60 minutes, then reacted with a mixed solution of propylene oxide/EPON Resin (1:3) at room temperature overnight, further reacted with EPON Resin at 30° C. overnight and embedded, and then subjected to polymerization reaction at 60° C. for 2 days.

The prepared samples were sliced to a thickness of 200 to 300 nm with a Leica EM UC-7, mounted on slide glasses, extended at 80° C. for 1 to 2 minutes, stained with toluidine blue (FUJIFILM Wako Pure Chemical Corporation; 535-05542) at 80° C. for 1 to 2 minutes. The samples were observed with an optical microscope, portions observed by an electron microscope were selected, and the blocks were trimmed and then sliced to a thickness of 80 nm by Leica EM UC-7. The sliced specimens were placed on a grid, dried, reacted with 2% uranium acetate solution (FUJIFILM Wako Pure Chemical Corporation; 219-00692) for 8 minutes, and a mixed solution containing 1% lead acetate (TAAB Laboratories Equipment Ltd.; L021)/1% lead nitrate (TAAB Laboratories Equipment Ltd.; L018)/1% lead citrate (TAAB Laboratories Equipment Ltd.; L019) for 4 minutes. After drying, observation was performed at an accelerating voltage of 80 kV using a transmission electron microscope (H-7600, Hitachi High-Tech Corporation).

Figure 16A:
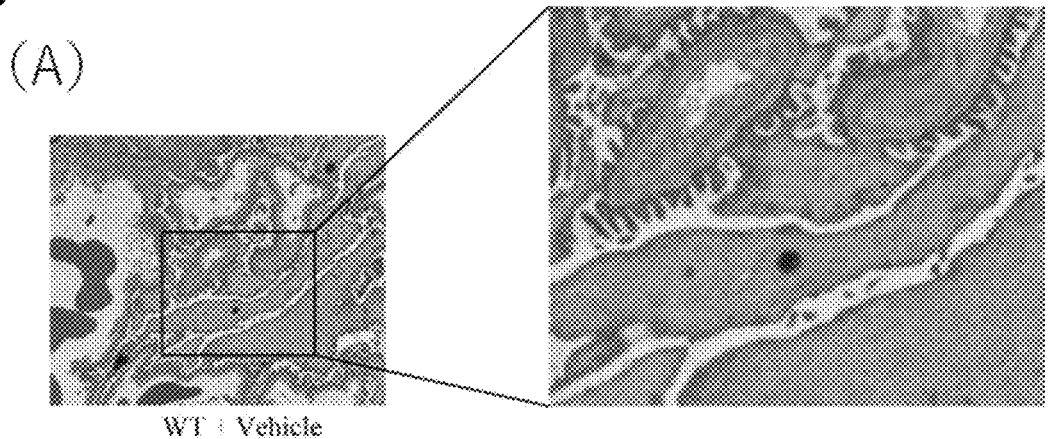
FIG. 16A is photographs showing the result obtained by observing a kidney tissue of a mouse in a wild type group by a transmission electron microscope.
Figure 16B:
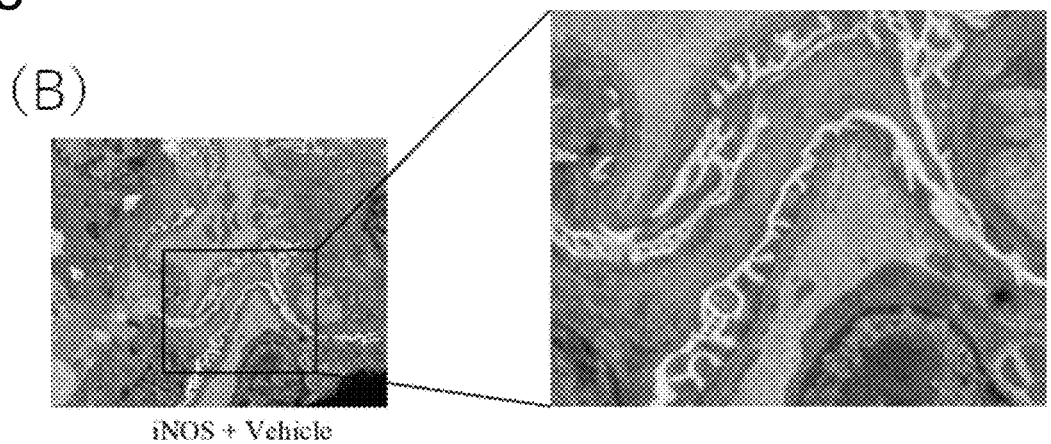
FIG. 16B is photographs showing the result obtained by observing a kidney tissue of a model mouse in a non-administered group by a transmission electron microscope.
Figure 16C:
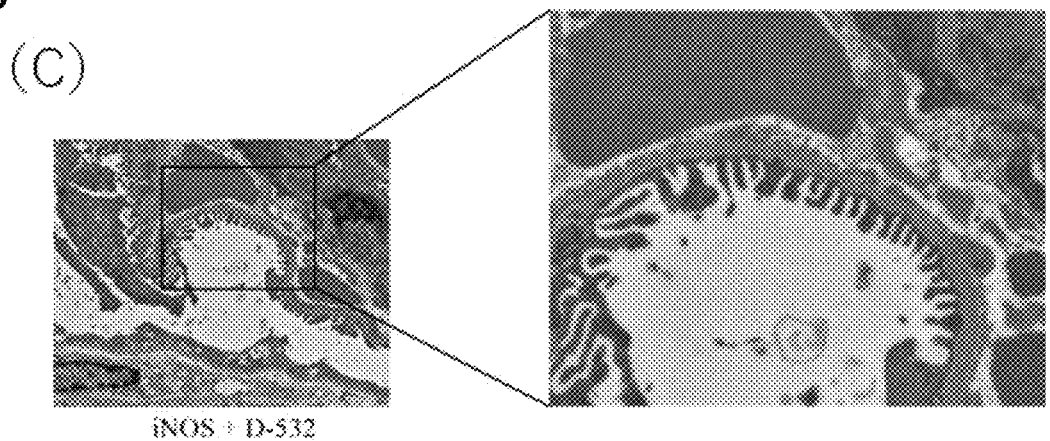
FIG. 16C is photographs showing the result obtained by observing a kidney tissue of a model mouse in a D-532-administered group by a transmission electron microscope.
Figure 17:
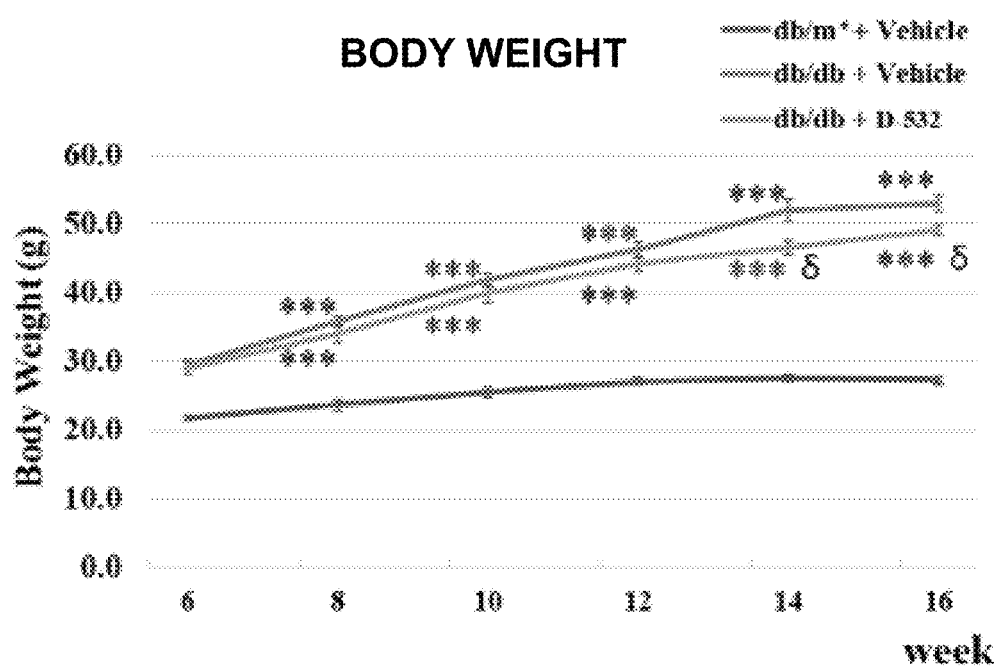
FIG. 17 is a graph showing the transition of the average weights of db/db mice in groups. With respect to a db/m+ mouse group, it is meant that ***: p<0.001. With respect to a non-administered group of db/db mice, it is meant that δ: p<0.05.
Figure 18:
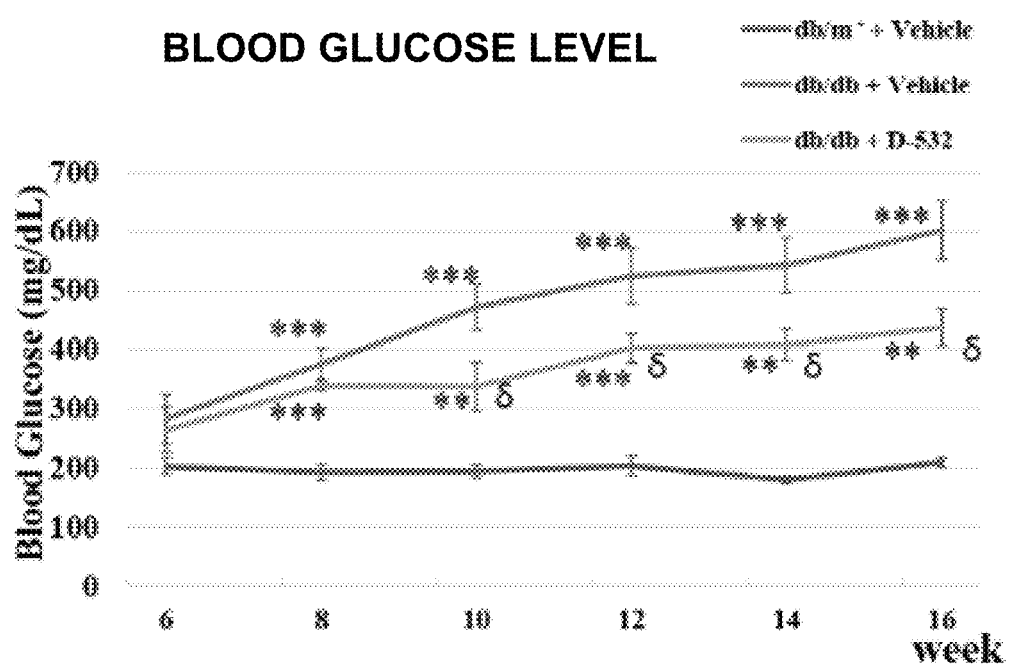
FIG. 18 is a graph showing the transition of the blood sugar levels of db/db mice in groups (average values). With respect to a db/m+ mouse group, it is meant that : p<0.01, and *: p<0.001. With respect to a non-administered group of db/db mice, it is meant that δ: p<0.05.
Figure 19:
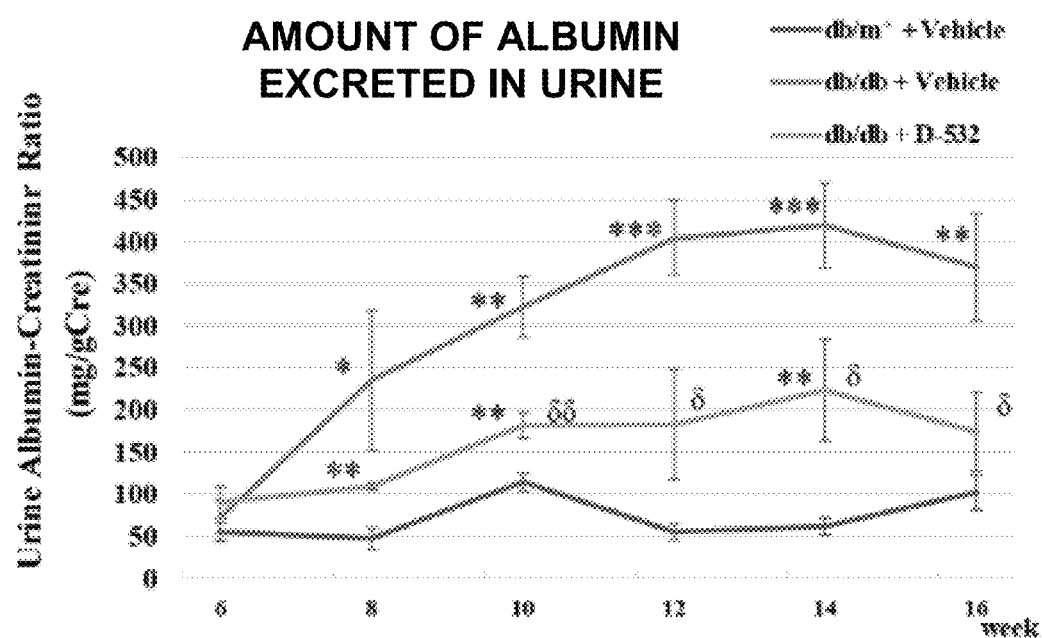
FIG. 19 is a graph showing the transition of the amounts of albumin excreted in urine of mice in groups (average values). With respect to a db/m+ mouse group, it is meant that *: p<0.05, : p<0.01, and *: p<0.001. With respect to a non-administered group of db/db mice, it is meant that δ: p<0.05, and δδ: p<0.01.
Figure 20:
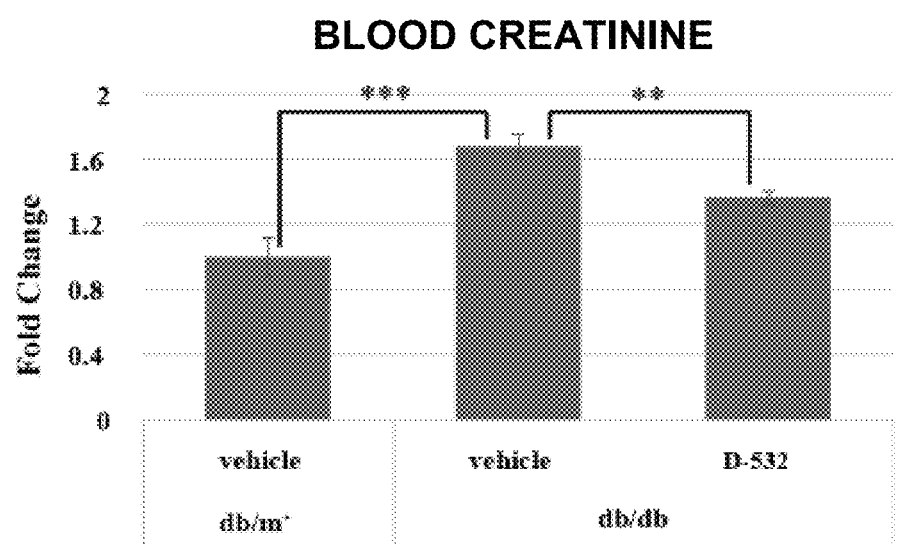
FIG. 20 is a graph showing the measurement results of the blood creatinine levels measured at the time of mouse dissection. It is meant that : p<0.01, and *: p<0.001.
Figure 21:
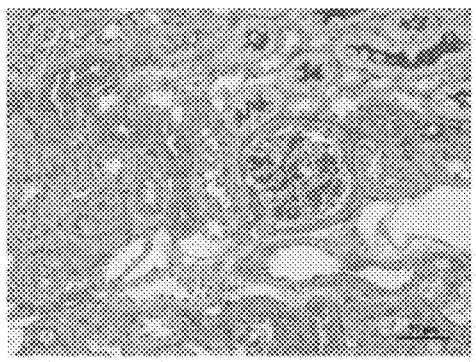
FIG. 21 is photomicrographs of kidney tissues stained with PAS and a graph showing the PAS-positive area ratios in glomeruli. It is meant that ***: p<0.001.
Figure 21:
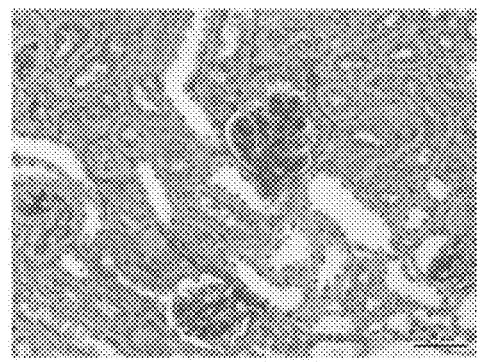
Figure 21:
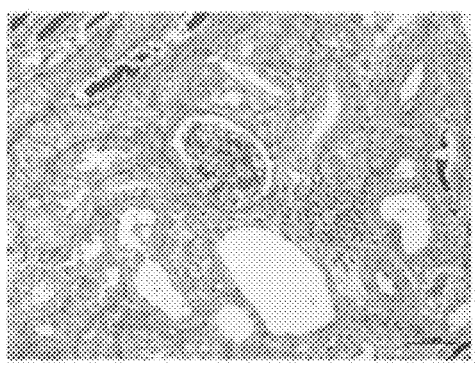
Figure 21:
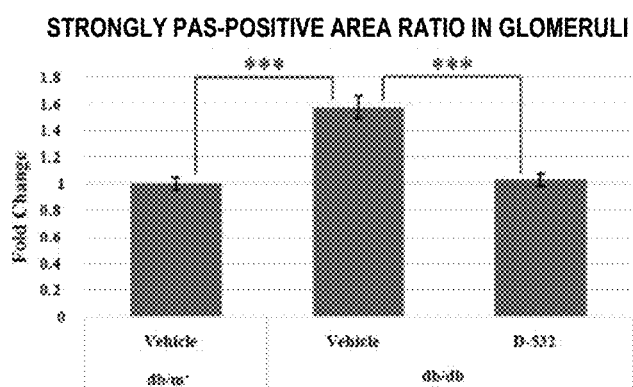

Although regular engaging structure can be observed in foot processes of the wild type mouse (WT+Vehicle, FIG. 16A), the regular structure observed in the wild type mouse changed, and the conglutination and disappearance of the foot processes were observed in foot processes of the type I diabetic mouse developing diabetic nephropathy (iNOS+Vehicle, FIG. 16B), Meanwhile, the regular engaging structure could be observed in foot processes of the type I diabetic mouse to which D-532 was administered (iNOS+D-532, FIG. 16C). This shows that D-532 suppressed the structural change of the foot processes accompanying the development and progress of diabetic nephropathy. It is known that foot processes have an important role of filters of blood, and it is considered that the prevention of the conglutination and disappearance of foot processes accompanying diabetic nephropathy also has great significance from the viewpoint of preventing the deterioration of renal function.

[Test Example 7] Test Using Db/Db Mice db/db mice (obtained by mating hetero mice (db/m+)) was used as model mice. Tests were performed under the same conditions as in Test Example 3 using 16-week-old model mice (experimental group n=8, control group n=6) and a wild type group (n=8) which are hetero mice (db/m+) (purchased from Kumagai-shigeyasu Co., Ltd.), and the results were analyzed and observed. FIG. 17 to FIG. 21 shows the results. The same effect as the effect observed using the model mice described in Test Example 3 (FIG. 3 to FIG. 6, and FIG. 9) was also confirmed when the db/db mice were used.

[Test Example 8] Test Using Db/Db Mice

Figure 22:
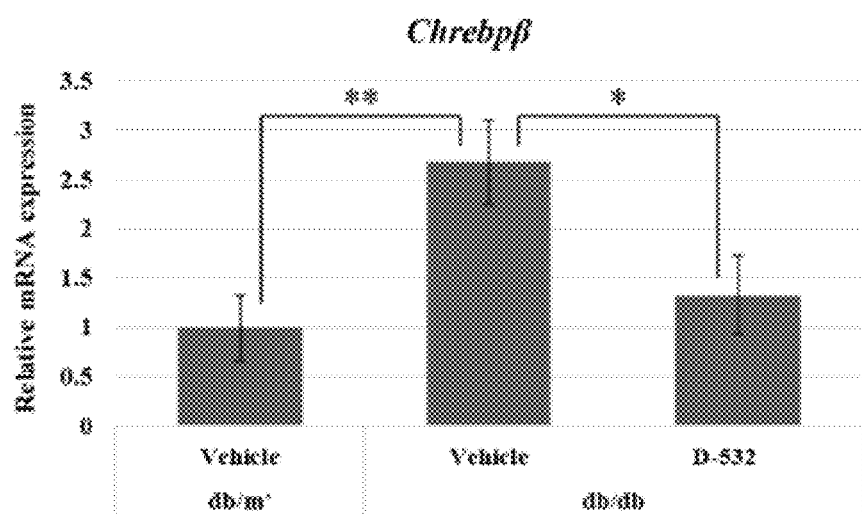
FIG. 22 is a graph showing the results obtained by analyzing the expression variations of the ChREBPβ gene, which is a target gene of ChREBP, in the kidney by quantitative PCR. It is meant that *: p<0.05, and **: p<0.01.
Figure 23:
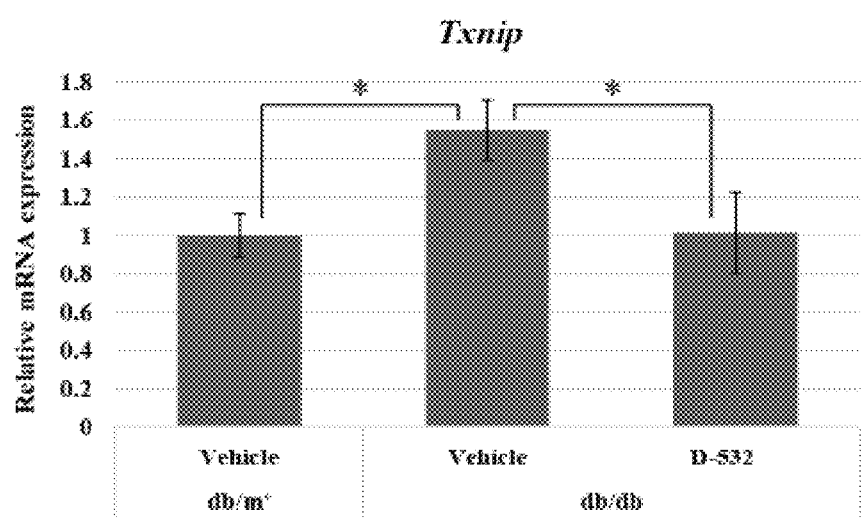
FIG. 23 is a graph showing the results obtained by analyzing the expression variations of the TXNIP gene, which is a target gene of ChREBP, in the kidney by quantitative PCR. It is meant that *: p<0.05.

In the mice used in Test Example 7, ChREBP target gene expression analysis was performed by the same method as in Test Example 4. FIG. 22 and FIG. 23 show the results. Decrease in the expression by D532 administration was observed as to ChREBPβ and TXNIP.

[Test Example 9] Observation of Mouse Glomeruli

Figure 24A:
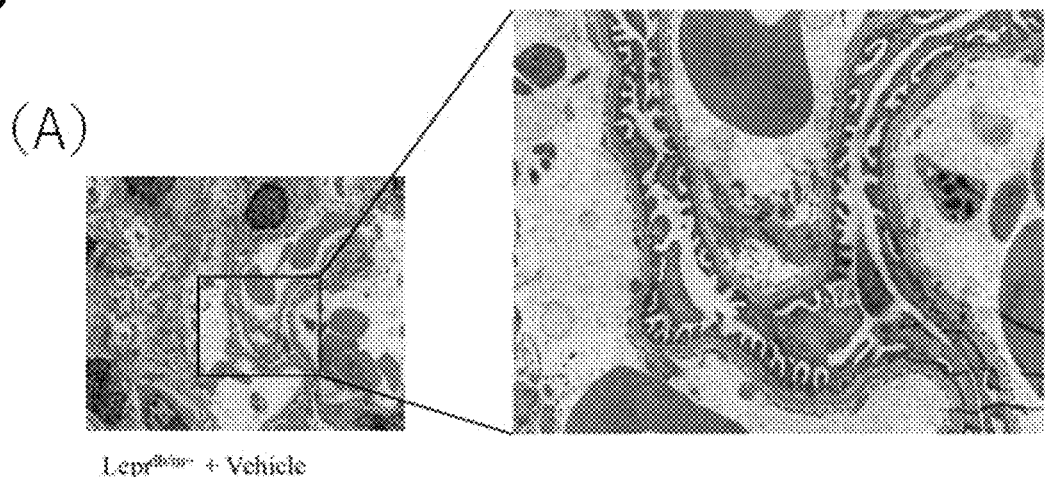
FIG. 24A is photographs showing the result obtained by observing a kidney tissue of a hetero mouse (db/m+) by a transmission electron microscope.
Figure 24B:
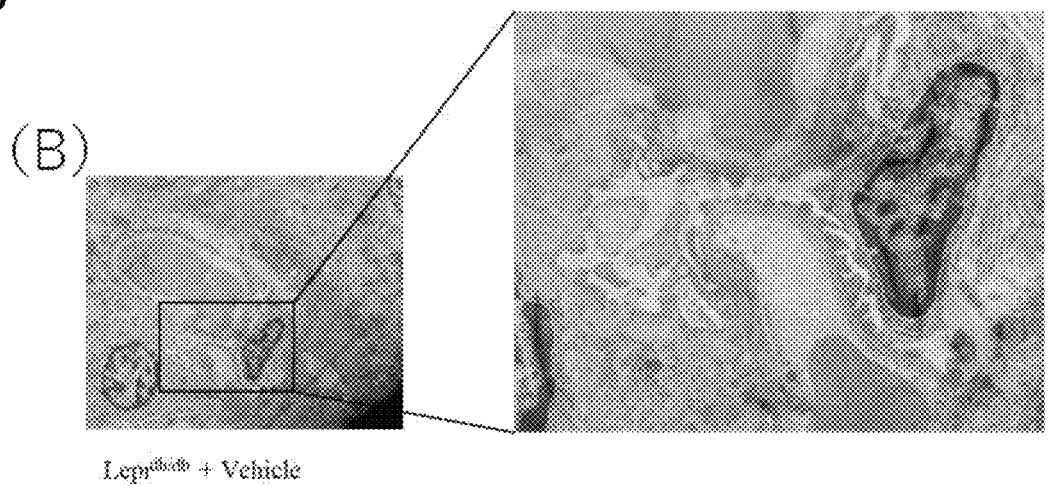
FIG. 24B is photographs showing the result obtained by observing a kidney tissue of a db/db mouse in a non-administered group by a transmission electron microscope.
Figure 24C:
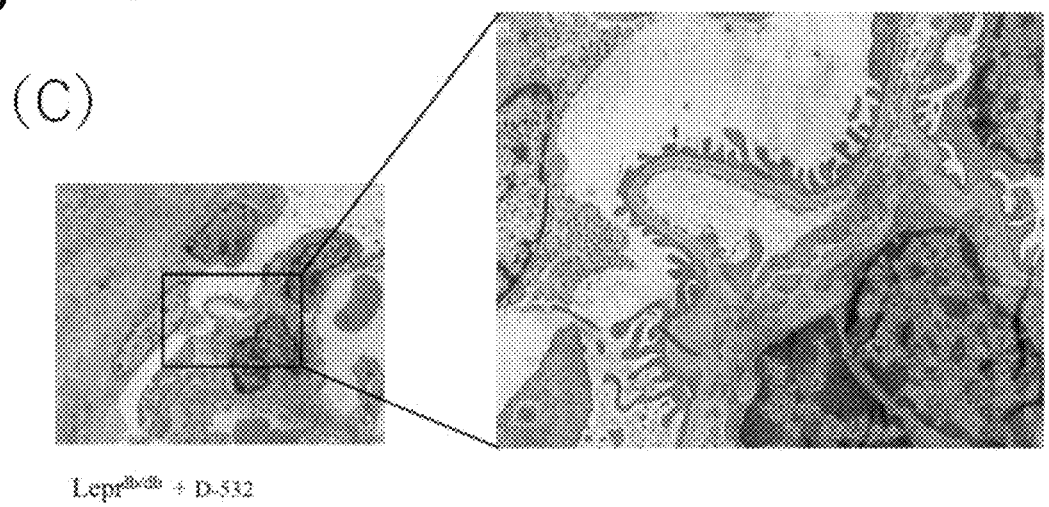
FIG. 24C is photographs showing the result obtained by observing a kidney tissue of a db/db mouse in a D-532-administered group by a transmission electron microscope.

In the mice used in Test Example 7, the kidney tissues were observed by the same method as in Test Example 6. FIGS. 24A to C show the results. In the db/db mice, the same effect as the effect observed in the iNOS mice (the above-mentioned FIG. 16) was also confirmed.

The effect of the compound of the present invention was confirmed in both the test results using the iNOS mice generally understood also as a type I diabetic model and the test results using the db/db mice generally understood also as a type II diabetic model. This showed that the compound of the present invention has preventive and therapeutic effects on diabetic nephropathy developed as a complication regardless of the type of diabetes.

Figure 25:
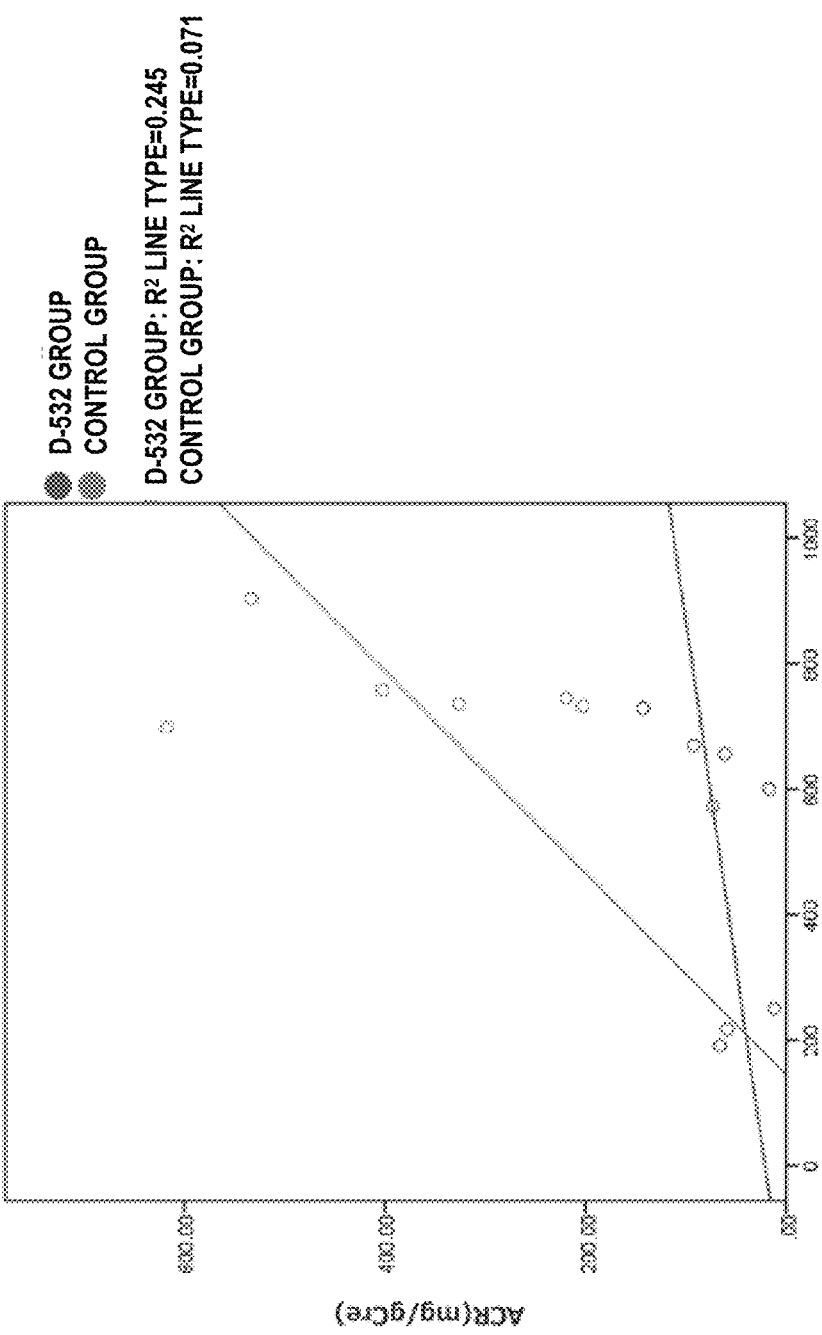
FIG. 25 is a graph showing the results obtained by creating a scatter diagram as to the blood sugar levels and the amounts of albumin excreted in urine (ACR) of an experimental group and a control group in Test Example 7 using SPSS, which is statistical analysis software, so that the abscissa axis is the blood sugar level, and the ordinate axis is the ACR and finding regression lines (linear approximation by the least squares method).

[Test Example 10] as to Graph of Relationship Between Blood Sugar Level and Proteinuria As to the blood sugar levels and the amounts of albumin excreted in urine (ACR) of the experimental group and the control group (non-administered group of db/db mice) in Test Example 7, a scatter diagram was created using SPSS, which is statistical analysis software, so that the abscissa axis is the blood sugar level, and the ordinate axis is the ACR, and regression lines (linear approximation by the least squares method) were found. FIG. 25 shows the results. Since the control group and the experimental group are greatly different in the gradient of the regression line, it is considered that the effect of D-532 on ACR is significant with respect to an effect of reducing the blood sugar level, namely D-532's effect of improving the ACR (effect of protecting the kidney) is not indirect change accompanying an effect of reducing the blood sugar level, and D-532 have a direct effect on the kidney.

The invention claimed is:

1. A compound represented by chemical formula (I):

[Chemical Formula 1]

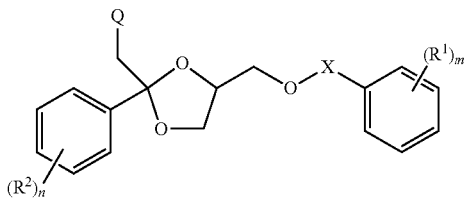
(I)

wherein $R^1$ and $R^2$ are each independently selected from a halogen atom, hydroxy, $C_{1-6}$ alkyl, and $C_{1-6}$ alkoxy;

m and n are each independently an integer selected from 0 to 5; X is —$CH_2$— or —C(=O)—; and Q is a nitrogen-containing 5-membered heteroaryl condensed with a benzene ring, the heteroaryl attaching via a ring nitrogen atom, or a pharmaceutically acceptable salt thereof.

2. The compound according to claim 1, wherein X is —$CH_2$—, or a pharmaceutically acceptable salt thereof.

3. The compound according to claim 1, wherein the compound is represented by chemical formula (Ia):

[Chemical Formula 2]

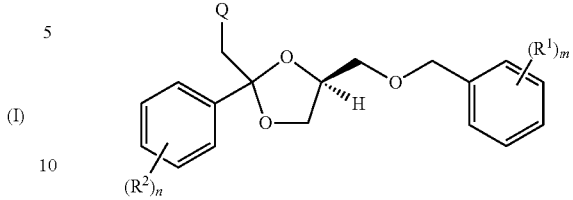
(Ia)

wherein $R^1$, $R^2$, m, n, and Q are as already defined, or a pharmaceutically acceptable salt thereof.

4. The compound according to claim 1, wherein n is an integer selected from 0 to 2, and $R^2$ is a halogen atom, or a pharmaceutically acceptable salt thereof.

5. The compound according to claim 1, wherein m is 0, or a pharmaceutically acceptable salt thereof.

6. The compound according to claim 1, wherein Q is 1,2,3-benzotriazol-1-yl, or a pharmaceutically acceptable salt thereof.

7. The compound according to claim 1, wherein the compound is: 1 (((2S,4S)-4-((benzyloxy)methyl)-2-phenyl-1,3-dioxolan-2-yl)methyl)-1H-benzo[d] [1,2,3]triazole or a pharmaceutically acceptable salt thereof.

8. A pharmaceutical composition comprising the compound according to claim 1 or a pharmaceutically acceptable salt thereof.

9. The pharmaceutical composition according to claim 8, for use in treating a disease selected from diabetic nephropathy, glomerular injury, tubular injury, renal injury accompanying advanced age or related to dialysis, nephrosclerosis, nephrotoxicity, renal ischemia, primary vesicoureteral reflux, glomerulosclerosis, IgA-induced nephropathy, and hypertension-induced nephropathy.

* * * * *